United States Patent
Wang et al.

(10) Patent No.: US 10,851,062 B2
(45) Date of Patent: *Dec. 1, 2020

(54) SUBSTITUTED HETEROARYL COMPOUND, COMPOSITION CONTAINING SAME, AND APPLICATION THEREOF

(71) Applicant: Shenzhen TargetRx, Inc., Guangdong (CN)

(72) Inventors: Yihan Wang, Guangdong (CN); Xingye Ren, Shenzhen (CN)

(73) Assignee: Shenzhen TargetRx, Inc., Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/686,523

(22) Filed: Nov. 18, 2019

(65) Prior Publication Data

US 2020/0190036 A1 Jun. 18, 2020

Related U.S. Application Data

(63) Continuation of application No. 16/079,880, filed as application No. PCT/CN2016/109673 on Dec. 13, 2016, now Pat. No. 10,479,767.

(30) Foreign Application Priority Data

Feb. 28, 2016 (CN) .......................... 2016 1 0108096
Jul. 11, 2016 (CN) .......................... 2016 1 0538562

(51) Int. Cl.

| C07D 217/24 | (2006.01) |
| A61K 31/472 | (2006.01) |
| C07D 217/26 | (2006.01) |
| C07B 59/00 | (2006.01) |
| A61K 31/438 | (2006.01) |
| A61P 7/06 | (2006.01) |

(52) U.S. Cl.
CPC .......... *C07D 217/26* (2013.01); *A61K 31/438* (2013.01); *A61P 7/06* (2018.01); *C07B 59/002* (2013.01); *C07B 2200/05* (2013.01)

(58) Field of Classification Search
CPC ............................ C07D 217/24; A61K 31/472
USPC .......................................... 546/141; 514/309
See application file for complete search history.

(56) References Cited

U.S. PATENT DOCUMENTS

| 7,323,475 B2 | 1/2008 | Arend |
| 10,479,767 B2 | 11/2019 | Wang et al. |
| 2004/0235082 A1 | 11/2004 | Fourney et al. |
| 2006/0199836 A1 | 9/2006 | Turtle et al. |
| 2007/0037815 A1 | 2/2007 | Tung |

FOREIGN PATENT DOCUMENTS

| CN | 1720051 A | 1/2006 |
| CN | 1816527 A | 8/2006 |
| CN | 106083720 A | 11/2016 |
| EP | 1644336 | 4/2006 |
| EP | 2144903 | 1/2010 |
| EP | 2357175 A | 8/2011 |
| EP | 3415502 | 12/2018 |
| JP | 2006-527200 A | 11/2006 |
| JP | 2008-531736 A | 8/2008 |
| JP | 2009-502961 A | 1/2009 |
| JP | 2010-523694 A | 7/2010 |
| WO | WO 2004/108681 A1 | 12/2004 |
| WO | WO 2007/090068 A2 | 8/2007 |
| WO | WO 2008/124803 A1 | 10/2008 |

OTHER PUBLICATIONS

[No Author Listed] Organic Square Wako. Sep. 2010. No. 33.
RN 1794767-9303. Jul. 5, 2015.
Aik et al., Structural basis for inhibition of the fat mass and obesity associated protein (FTO). J Med Chem. May 9, 2013;56(9):3680-8. doi:10.1021/jm400193d. Epub Apr. 23, 2013.
Buteau, Deuteraed drugs: unexpectedly nonobvious? J High Tech I. 2009;22-74.
Harbeson et al., Deuterium in Drug Discovery and Development. Annual Rep Med Chem. 2011;46:403-417.
Shao et al., Derivatives of tramadol for increased duration of effect. Bioorg Med Chem Lett. Feb. 2006;16(3):691-4. Epub Oct. 27, 2005.

*Primary Examiner* — Charanjit Aulakh
(74) *Attorney, Agent, or Firm* — Wolf, Greenfield & Sacks, P.C.

(57) ABSTRACT

Provided in the present invention are a substituted heteroaryl compound, a composition containing same, and an application thereof, the present invention disclosing a heteroaryl compound of the formula (I), or a crystalline form, a pharmaceutically acceptable salt, a prodrug, a stereoisomer, a hydrate, or a solvent compound thereof. The substituted heteroaryl compound and the composition containing same set forth in the present invention can be used for regulating hypoxia inducible factor (HIF) and/or endogenous erythropoietin (EPO), simultaneously having better pharmacokinetic parameter characteristics and being able to improve the drug concentration of the compound in animal bodies, in order to improve the curative effect and safety of the drug.

19 Claims, No Drawings

SUBSTITUTED HETEROARYL COMPOUND, COMPOSITION CONTAINING SAME, AND APPLICATION THEREOF

CROSS REFERENCE TO RELATED APPLICATIONS

This application is a continuation of U.S. application Ser. No. 16/079,880, filed Aug. 24, 2018, which is a national stage filing of International Patent Application No. PCT/CN2016/109673, filed Dec. 13, 2016, which claims priority to Chinese patent application numbers 201610538562.0, filed Jul. 11, 2016, and 201610108096.2, filed Feb. 28, 2016, the entire contents of each of which are incorporated herein by reference.

FIELD OF THE PRESENT INVENTION

The present disclosure belongs to the pharmaceutical field, and in particular relates to a substituted heteroaryl compound and a composition comprising the same, as well as a method and compound capable of regulating the stability of hypoxia inducible factor (HIF) subunits and increasing endogenous erythropoietin in vitro and in vivo.

BACKGROUND OF THE PRESENT INVENTION

Hypoxia inducible factor (HIF) is a basic helix-loop-helix (bHLH) PAS (Per/Arnt/Sim) transcriptional activator that regulates changes in gene expression in response to changes in cellular oxygen concentration. HIF is a heterodimer containing an oxygen-regulated alpha subunit (HIFα) and a constitutively expressed beta subunit (HIFβ), also known as the aromatic hydrocarbon receptor nuclear transporter (ARNT). In oxygenated (normoxic) cells, the HIFα subunit is rapidly degraded by a mechanism involving the ubiquitination of the VonHipple-Lindau tumor suppressor (pVHL) E3 ligase complex. Under hypoxic conditions, HIFα does not degrade, and an active HIFα/β complex accumulates in the nucleus and activates expression of several genes, including glycolytic enzymes, glucose transporter (GLUT)-1, erythropoietin (EPO) and vascular endothelial growth factor (VEGF). (Maxwell et. al., Nature, 1999, 399, 271-275)

Erythropoietin (EPO) is a naturally occurring hormone produced in response to HIFα that stimulates the production of red blood cells that carry oxygen throughout the body. EPO is usually secreted by the kidneys, and endogenous EPO increases under conditions of reduced oxygen (hypoxia). All types of anaemia are characterized by a reduced ability of the blood to carry oxygen, and are therefore accompanied by similar signs and symptoms, including paleness of the skin and mucous membranes, weakness, dizziness, fatigue, and drowsiness, resulting in a decline in quality of life. Subjects with severe anaemia showed difficulty in breathing and heart malformations. Anemia is usually associated with a condition in which the blood is deficiency in red blood cells or in hemoglobin.

Ischemic and hypoxic conditions arc main causes of morbidity and mortality. Cardiovascular disease causes at least 15 million deaths each year and is the cause of 30% of deaths in the world. Among various cardiovascular diseases, ischemic heart disease and cerebrovascular disease cause about 17% of deaths. There are 1.3 million cases of non-fatal acute myocardial infarction reported each year, constituting an incidence of approximately 300 per 100,000 people. On the other hand, it is estimated that 5 million Americans suffer from venous phlebothrombosis each year, and about 600,000 of these cases cause pulmonary embolism. About one-third of patients with pulmonary embolism eventually die, making pulmonary embolism the third most common cause of death in the United States.

Currently, the treatment of ischemic and hypoxic conditions focuses on the relief of symptoms and the treatment of pathological conditions. For example, treatment of myocardial infarction includes nitroglycerin and analgesics to control pain and relieve the workload of the heart. Other medications including digoxin, diuretics, amrinone, beta-blockers, lipid-lowering agents, and angiotensin-converting enzyme inhibitors are used to stabilize the condition, but none of these therapies can directly act on tissue damage caused by ischemia and hypoxia.

Due to the current deficiencies in the treatment and in the production and use of recombinant EPO, there is still a need for compounds that are effective in treating erythropoietin-related conditions, such as anemia, including anemia associated with diabetes, anemia, ulcers, renal failure, cancer, infections, dialysis, surgery and chemotherapy, and conditions involving ischemia and hypoxia, such as arterial occlusive disease, angina pectoris, intestinal infarction, pulmonary infarction, cerebral ischemia, and myocardial infarction. There is also a need for compounds that effectively prevent tissue damage caused by ischemia, which occurs due to, for example, atherosclerosis, diabetes, and pulmonary disorders such as pulmonary embolism and the like. In summary, there is a need in the art for methods and compounds that modulate HIF and/or endogenous erythropoietin and that can be used to treat and prevent HIF-associated and EPO-associated disorders, including conditions associated with anaemia, ischemia, and hypoxia.

SUMMARY OF THE PRESENT INVENTION

In view of the above technical problems, disclosed herein are a compound and a composition comprising the same, which can be used for regulating hypoxia inducible factor (HIF) and/or endogenous erythropoietin (EPO) and/or having better pharmacodynamic/pharmacokinetic properties.

In this regard, the technical solution adopted herein is:

The object of the present disclosure is to provide a new class of compounds that can be used to modulate hypoxia inducible factor (HIF) and/or endogenous erythropoietin (EPO) and/or have better pharmacodynamic/pharmacokinetic properties.

In a first aspect, provided herein is a compound represented by Formula (I), or a crystal form, a pharmaceutically acceptable salt, a hydrate or a solvate thereof, Formula (I)

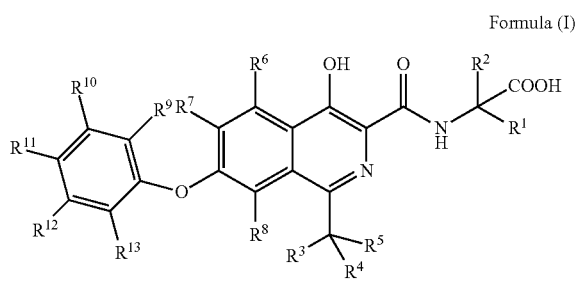

wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are each independently hydrogen, deuterium, halogen;

provided that at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is deuterated or deuterium.

In another embodiment, $R^1$ and $R^2$ are each independently deuterium or hydrogen.

In another embodiment, $R^1$ and $R^2$ are deuterium.

In another embodiment, $R^3$, $R^4$, and $R^5$ are each independently deuterium or hydrogen.

In another embodiment, $R^6$, $R^7$, and $R^8$ are each independently deuterium or hydrogen.

In another embodiment, $R^9$, $R^{10}$, $R^{11}$, $R^{12}$, and $R^{13}$ are each independently deuterium or hydrogen.

In another embodiment, the compound may be selected from, but not limited to, the group consisting of the following compounds, or pharmaceutically acceptable salts thereof:

Formula (2)

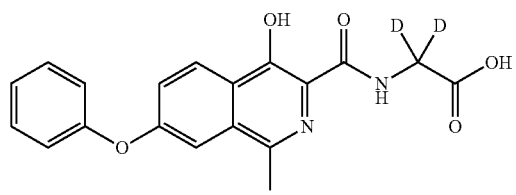

Formula (3)

Formula (4)

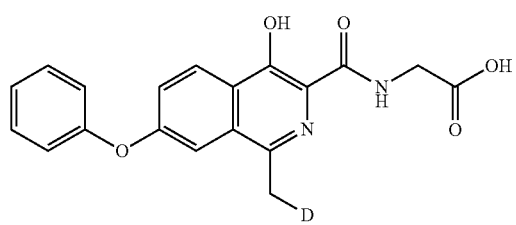

Formula (5)

Formula (6)

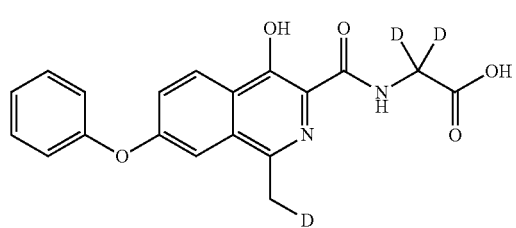

-continued

Formula (7)

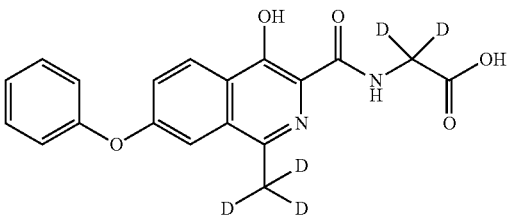

Formula (8)

Formula (9)

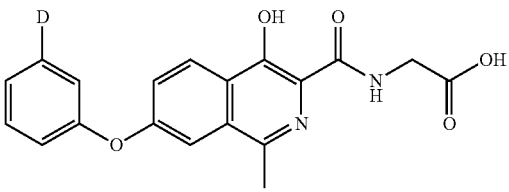

Formula (10)

Formula (11)

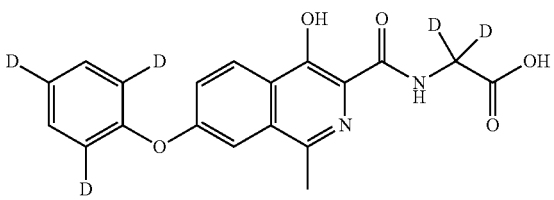

Formula (12)

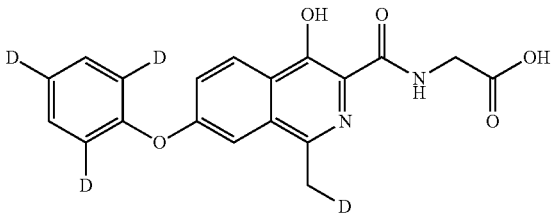

Formula (13)

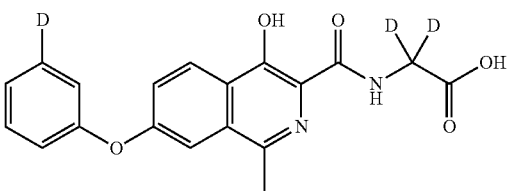

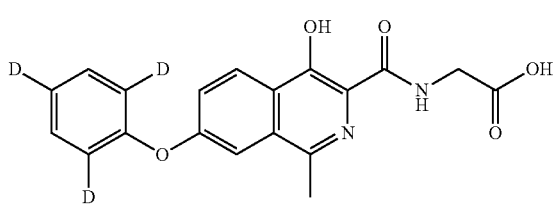

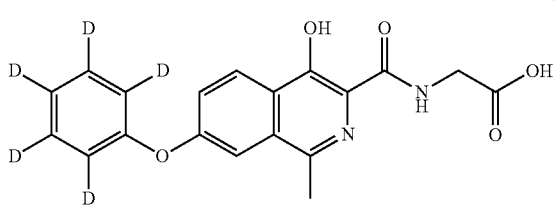

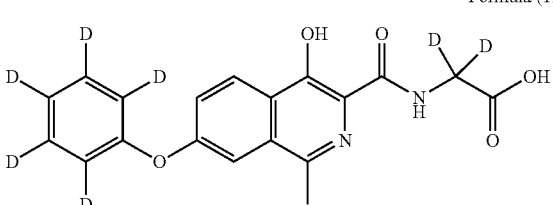

-continued
Formula (14)
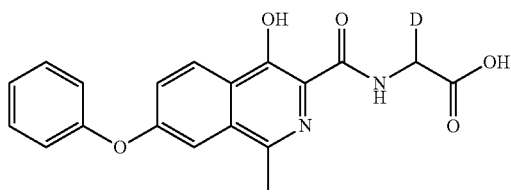
Formula (15)
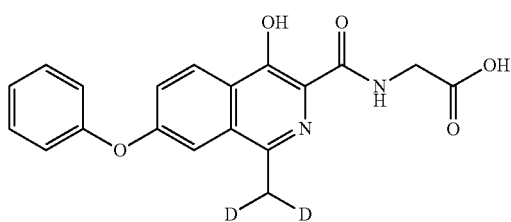
Formula (16)
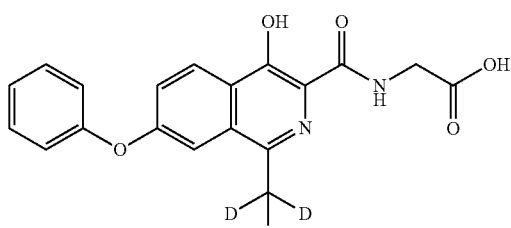
Formula (17)
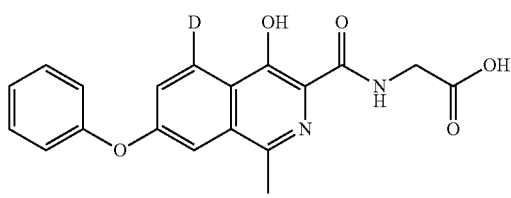
Formula (18)
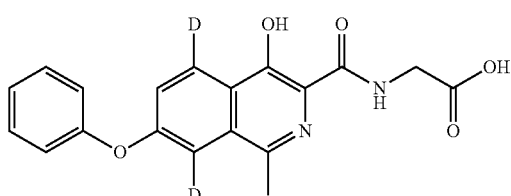
Formula (19)
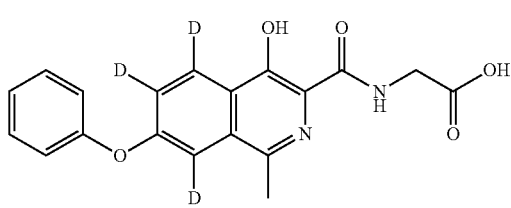
Formula (20)
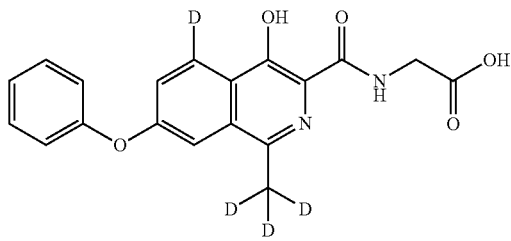
-continued
Formula (21)
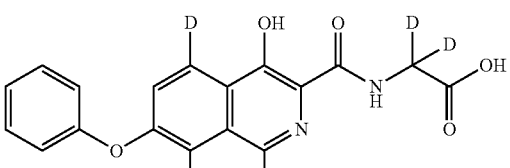
Formula (22)
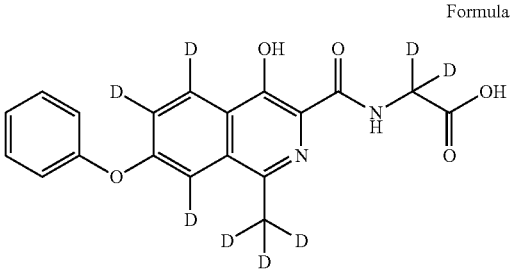
Formula (23)
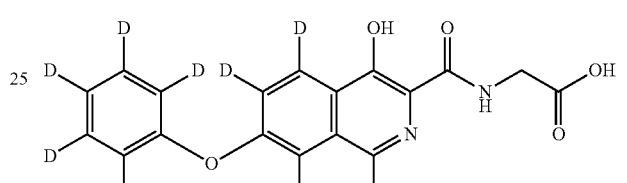
Formula (24)
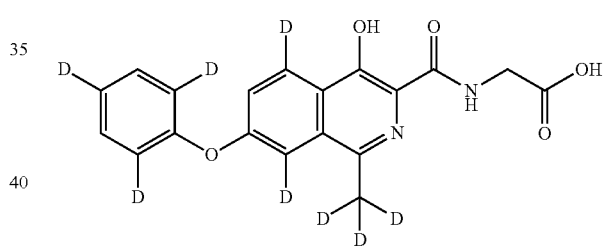
Formula (25)
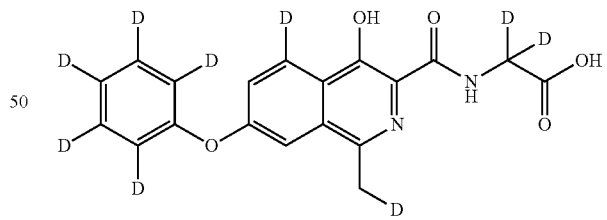
Formula (26)
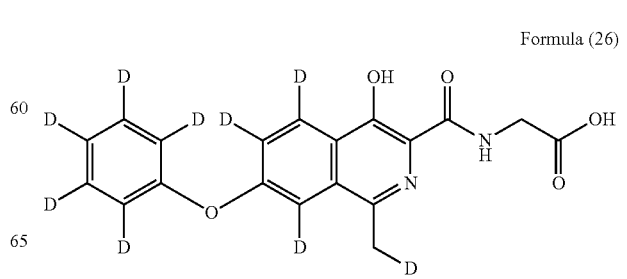

-continued

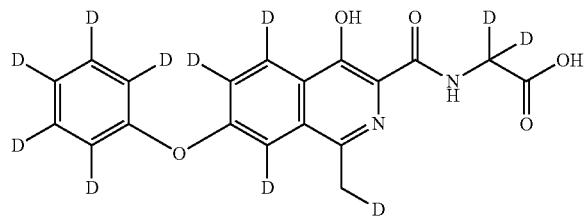

Formula (27)

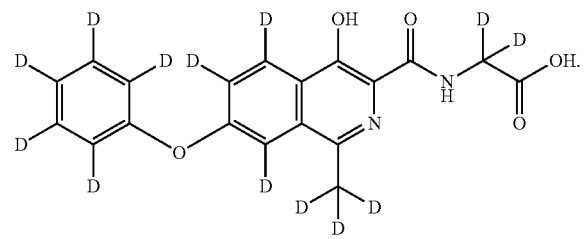

Formula (28)

In another embodiment, the content of the deuterium isotope at the deuterated position is at least greater than the natural content of the deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$ and $R^{13}$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and even more preferably greater than 99%.

In another embodiment, in $R^1$, $R^2$, $R^3$, $R^4$, $R^5$, $R^6$, $R^7$, $R^8$, $R^9$, $R^{10}$, $R^{11}$, $R^{12}$ and $R^{13}$ of the compound of Formula (I), at least one R contains deuterium, and more preferably two Rs, more preferably three Rs, more preferably four Rs, more preferably five Rs, more preferably six Rs, more preferably seven Rs, more preferably eight Rs, more preferably nine Rs, more preferably ten Rs, more preferably eleven Rs, more preferably twelve Rs, and more preferably thirteen Rs contain deuterium.

In another embodiment, the compound does not include a non-deuterated compound.

In the second aspect, provided herein is a method for preparing a pharmaceutical composition comprising the step of: mixing a pharmaceutically acceptable carrier and the compound, or a crystal form, a pharmaceutically acceptable salt, a hydrate or a solvate thereof as described in the first aspect disclosed herein to form a pharmaceutical composition.

In a third aspect, provided herein is a pharmaceutical composition comprising a pharmaceutically acceptable carrier and the compound, or a crystal form, a pharmaceutically acceptable salt, a hydrate or a solvate thereof as described in the first aspect disclosed herein.

Pharmaceutically acceptable carriers that can be used in the pharmaceutical compositions disclosed herein include, but are not limited to, any glidants, sweeteners, diluents, preservatives, dyes/colorants, flavor enhancers, surfactants, moisturizing agents, dispersants, disintegrants, suspending agents, stabilizers, isotonic agents, solvents or emulsifiers.

The pharmaceutical composition disclosed herein can be formulated into solid, semi-solid, liquid or gaseous formulations, such as tablets, pills, capsules, powders, granules, ointments, emulsions, suspensions, solutions, suppositories, injections, inhalants, gels, microspheres, aerosols and the like.

Typical routes of administration of the pharmaceutical compositions disclosed herein include, but are not limited to, oral, rectal, transmucosal, enteral, topical, transdermal, inhalation, parenteral, sublingual, intravaginal, intranasal, intraocular, intraperitoneal, intramuscular, subcutaneous, and intravenous administration. Oral administration or injection administration is preferred.

The pharmaceutical composition disclosed herein may be manufactured by methods known in the art, such as conventional mixing methods, dissolution methods, granulation methods, sugar-coated pills making methods, fine grinding methods, emulsification methods, freeze-drying methods, and the like.

It should be understood that within the scope of the present disclosure, the above technical features disclosed herein and the technical features specifically described in the following (such as examples) can be combined with each other to constitute a new or preferred technical solution. Due to space limitations, they will not be repeated here exhaustively.

As used herein, "halogen" means F, Cl, Br, and I unless otherwise specified.

More preferably, a halogen atom is selected from F, Cl and Br.

As used herein, unless otherwise specified, "deuterated" means that one or more hydrogens in a compound or group is replaced by deuterium; deuterated may be mono-substituted, di-substituted, multi-substituted or fully substituted by deuterium. The terms "substituted with one or more deuteriums" and "deuterated one or more times" are used interchangeably.

As used herein, unless otherwise specified, "non-deuterated compound" means a compound containing deuterium in an atomic ratio that is not higher than the natural content of a deuterium isotope (0.015%).

Also disclosed herein are isotopically labeled compounds to the extent of the original compounds disclosed herein. Examples that can be listed as isotopes of compounds disclosed herein include hydrogen, carbon, nitrogen, oxygen, phosphorus, sulfur, fluorine, and chlorine isotopes, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds, or enantiomers, diastereomers, isomers, or pharmaceutically acceptable salts or solvates disclosed herein, in which the above isotopes or other isotopes are contained are within the scope of the present disclosure. Certain isotopically labeled compounds disclosed herein, such as the radioisotopes of $^3H$ and $^{14}C$, are also among them and are useful in the tissue distribution experiments of drugs and substrates. Tritium, i.e., $^3H$ and carbon-14, i.e., $^{14}C$, are easier to be prepared and detected and are the first choice for isotopes. Isotopically-labeled compounds can be prepared using the schemes shown in the Examples by conventional methods by replacing non-isotopic reagents with readily available isotopically labeled reagents.

Pharmaceutically acceptable salts include inorganic and organic salts. A preferred class of salts is the salt formed by the compound disclosed herein with an acid. Acids suitable for formation of salts include, but are not limited to: inorganic acids such as hydrochloric acid, hydrobromic acid, hydrofluoric acid, sulfuric acid, nitric acid, phosphoric acid; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluenesulfonic acid, benzenesulfonic acid, naphthalenesulfonic acid; amino acids such as proline, phenylalanine, aspartic acid, and glutamic acid. Another preferred class of salt is a salt of a compound disclosed herein with a base such as an alkali metal salt (e.g., sodium or potassium salt), an alkaline earth metal salt (e.g., magnesium salt or calcium salt), an ammonium salt (e.g., a lower alkanolammonium salt and other pharmaceutically acceptable amine salts) such as methylamine salt, ethylamine salt, propylamine salt, dimethylamine salt, trimethylamine salt, diethylamine salt, triethylamine salt, tert-butylamine salt, ethylenediamine salt, hydroxyethylamine salt, dihydroxyethylamine salt, triethanolamine salt, and amine salts formed from morpholine, piperazine, and lysine, respectively.

The term "solvate" refers to a complex in which a compound disclosed herein coordinates with a solvent molecule in a particular ratio. "Hydrate" refers to a complex formed by coordination of a compound disclosed herein with water.

Disclosed herein is a method of modulating HIF and/or EPO which comprises stabilizing HIF and activating the expression of HIF-regulated genes by inhibiting HIFα hydroxylation. The method can also be applied to prevent, pre-treat or treat HIF- and/or EPO-related conditions, including anemia, ischemia, and hypoxic conditions.

Ischemia and hypoxia are two conditions associated with HIF and include, but are not limited to, myocardial infarction, hepatic ischemia, renal ischemia, and stroke; peripheral vascular disorders, ulcers, burns, and chronic wounds; pulmonary embolism; and ischemia-reperfusion injury, including, for example, ischemia-reperfusion injury associated with surgery and organ transplantation.

One aspect disclosed herein provides methods for treating various conditions of ischemia and hypoxia, particularly using the compounds described herein. In one embodiment, the method disclosed herein produces a therapeutic benefit when administered after ischemia or hypoxia. For example, after myocardial infarction, the methods disclosed herein dramatically reduce morbidity and mortality, and significantly improve cardiac structure and performance. On the other hand, the method disclosed herein improves liver function when administered after hepatotoxic-ischemic injury. Hypoxia is an important component of liver disease, especially in chronic liver disease associated with hepatotoxic compounds such as ethanol. In addition, gene expression induced by HIFα is known to increase in alcoholic liver disease, such as nitric oxide synthase and glucose transporter-1.

Accordingly, disclosed herein is a method of treating a condition associated with ischemia or hypoxia, comprising administering to a subject a therapeutically effective amount of a compound or a pharmaceutically acceptable salt thereof alone or in combination with a pharmaceutically acceptable excipient. In one embodiment, the compound is administered immediately after the ischemic condition, such as myocardial infarction, pulmonary embolism, intestinal infarction, ischemic stroke, and renal ischemia-reperfusion injury. In another embodiment, the compound is administered to a patient diagnosed as having a condition associated with the development of chronic ischemia, such as cardiogenic cirrhosis, macular degeneration, pulmonary embolism, acute respiratory failure, neonatal respiratory distress symptoms and congestive heart failure.

Another aspect disclosed herein provides methods for treating patients having a risk of developing ischemic or hypoxic conditions using the compounds described herein, such as individuals at high risk of atherosclerosis. Risk factors for atherosclerosis include, for example, hyperlipidemia, smoking, hypertension, diabetes, hyperinsulinemia and abdominal obesity. Accordingly, disclosed herein is a method for preventing ischemic tissue damage, comprising administering to a patient in need thereof a therapeutically effective amount of a compound or a pharmaceutically acceptable salt thereof alone or in combination with a pharmaceutically acceptable excipient. In one embodiment, the compounds may be administered based on predisposing conditions such as hypertension, diabetes, arterial occlusive disease, chronic venous insufficiency, Raynaud's disease, chronic skin ulcers, sclerosis, congestive heart failure, and systemic sclerosis.

In one particular embodiment, the method is used to increase blood vessel formation and/or granulation tissue formation in damaged tissue, wounds, and ulcers. For example, the compounds disclosed herein have been shown to be effective in stimulating granulation tissue formation during wound healing. Granulation tissue contains newly formed leaky blood vessels and temporary plasma protein matrix, such as fibrinogen and plasma fibronectin. The release of growth factors from inflammatory cells, platelets, and activated endothelial cells stimulates the migration and proliferation of fibroblasts and endothelial cells in granulation tissue. An ulcer can occur if the vascularization or nerve stimulation is impaired. The method disclosed herein effectively promotes the formation of granulation tissue. Thus, disclosed herein is a method for treating a patient having tissue damage due to, for example, an infarct, having a wound induced by, for example, trauma or injury, or having a chronic wound or ulcer due to a certain condition (e.g., diabetes), comprising administering to a patient in need thereof a therapeutically effective amount of a compound, or a pharmaceutically acceptable salt thereof, alone or in combination with a pharmaceutically acceptable excipient.

Another aspect disclosed herein provides a method of pre-treating a subject with the compound disclosed herein to reduce or prevent the occurrence of tissue damage associated with ischemia or hypoxia. When administered immediately prior to a condition involving ischemia or hypoxia, the methods disclosed herein produce a therapeutic benefit. For example, the method disclosed herein was applied prior to the induction of myocardial infarction to show a statistically significant improvement in heart structure and performance. On the other hand, when administered immediately before and during ischemia-reperfusion injury, the method disclosed herein produces a therapeutic benefit, significantly reducing the diagnostic parameters associated with renal failure.

Therefore, disclosed herein is a method of pre-treating a subject to reduce or prevent tissue damage associated with ischemia or hypoxia, comprising administering a therapeutically effective amount of a compound or a pharmaceutically acceptable salt thereof, alone or with a pharmaceutically acceptable excipient to a patient with a history of an ischemic condition, such as a myocardial infarction, or a patient with an impending ischemic condition, such as angina pectoris. In another embodiment, the compound may be administered on the basis of physical parameters suggestive of possible ischemia, e.g., for individuals under general anesthesia or temporarily working at high altitudes. In yet another embodiment, the compound can be used in organ transplantation to pre-treat organ donors or to maintain a removed organ prior to transplantation into a subject.

Previous studies have shown that certain compounds used in the methods disclosed herein are potent inhibitors of procollagen prolyl 4-hydroxylase. Although it is recognized that the initial infarct or recovery of the wound requires the deposition of connective tissue within the area of necrosis, the present disclosure demonstrates no side effects for the treatment of scarring. Thus, based on the benefits provided by certain compounds disclosed herein in the treatment and prevention of hypoxic tissue damage and fibrosis, the present disclosure encompasses a "dual therapy" method of treating or preventing conditions involving ischemia or hypoxia, including ischemia or hypoxia associated with concurrent reactive fibrosis, such as myocardial infarction and consequent congestive heart failure. The method may use a compound that inhibits more than one 2-oxoglutarate dioxygenase having the same specificity or different specificities, such as HIF prolyl hydroxylase and procollagen prolyl 4-hydroxylase. Alternatively, the method may use a combination of compounds wherein each compound specifically inhibits only one 2-oxoglutarate dioxygenase, e.g., one compound specifically inhibits HIF prolyl hydroxylase and the second compound specifically inhibits procollagen prolyl 4-hydroxylase.

In one aspect, the compounds disclosed herein inhibit one or more 2-oxoglutarate dioxygenases. In one embodiment, the compound inhibits at least two family members of 2-oxoglutarate dioxygenase having the same or different specificities, such as HIF prolyl hydroxylase and HIF asparagine-hydroxylase. In another embodiment, the compound is specific for one 2-oxoglutarate dioxygenase, such as HIF prolyl hydroxylase, and shows little or no specificity for other family members.

The compound can be administered in combination with a variety of other therapeutic methods. In one embodiment, the compound is administered with another 2-oxoglutarate dioxygenase inhibitor, wherein the both compounds have different specificities for individual family members of 2-oxoglutarate dioxygenase. The two compounds may be administered at the same time in a ratio relative to one another. The determination of the proportion suitable for a given course of treatment or a particular subject is within the skill of the art. Alternatively, the two compounds may be administered continuously over the course of treatment, for example after myocardial infarction. In one particular embodiment, one compound specifically inhibits the activity of HIF prolyl hydroxylase, and the second compound specifically inhibits the activity of procollagen prolyl 4-hydroxylase. In another particular embodiment, one compound specifically inhibits the activity of HIF prolyl hydroxylase, and the second compound specifically inhibits the activity of HIF asparaginyl-hydroxylase. In another embodiment, the compound is administered with another therapeutic agent having a different mode of action, such as an ACE inhibitor (ACED, an angiotensin-II receptor blocker (ARB), statin, diuretic agents, digoxin, carnitine, etc.

Disclosed herein are methods for increasing endogenous erythropoietin (EPO). These methods can be applied in vivo, such as in plasma, or in vitro, for example in a conditioned cell culture medium. The present disclosure further provides methods for increasing endogenous EPO levels for preventing, pre-treating or treating EPO-related conditions including, for example, conditions associated with anemia and neurological disorders. Anemia-related conditions include, for example, acute or chronic kidney disease, diabetes, cancer, ulcers, viral infections (e.g., HIV, bacteria, or parasites), inflammation, and the like. Anemia conditions can further include conditions associated with procedure or treatment including, for example, radiation therapy, chemotherapy, dialysis, and surgery. Anemia-related disorders additionally include abnormal hemoglobin and/or erythrocytes, for example found in conditions such as microcytic anemia, hypochromic anemia, aplastic anaemia, and the like.

The present disclosure can be used to prophylactically or simultaneously increase endogenous EPO in a subject undergoing a particular treatment or procedure, such as HIV-infected anemic patients being treated with azidothymidine (zidovudine) or other reverse transcriptase inhibitors, anemic cancer patients receiving cyclic cisplatin- or non-cisplatin-containing chemotherapeutics, or anemic or non-anemic patients who are scheduled to undergo surgery. Methods for increasing endogenous EPO can also be used to prevent, pre-treat, or treat EPO-related conditions associated with nerve damage or degeneration of nerve tissue including, but not limited to, stroke, trauma, epilepsy, spinal cord injury, and neurodegenerative disorders.

In addition, the method can be used to increase endogenous EPO levels in anemic or non-anemic patients scheduled to undergo surgery to reduce the need for exogenous blood transfusions or to facilitate banking of blood prior to surgery. A small reduction in the hematocrit of the blood that typically occurs after autologous blood donation before surgery does not stimulate the increase in endogenous EPO or compensatory erythropoiesis. However, pre-operative stimulation of endogenous EPO will effectively increase red blood cell mass and autologous blood volume while maintaining higher hematocrit levels, and the method is specifically encompassed herein. In some surgical populations, particularly individuals with surgical blood loss of greater than 2 liters, the method disclosed herein can be applied to reduce allogeneic blood exposure.

The methods disclosed herein can also be used to enhance athletic performance, improve exercise capacity, and promote or enhance aerobic conditioning. For example, an athlete may use the method to promote training and the soldier may use the method to improve, for example, stamina and patience.

The methods disclosed herein have been shown to increase the content of endogenous erythropoietin in the culture medium in which cells are cultured in vitro and in the plasma of animals treated in vivo. Although the kidney is a major source of erythropoietin in the body, other organs, including the brain, liver and bone marrow, can and do synthesize erythropoietin upon proper stimulation. The use of the methods disclosed herein can increase the expression of endogenous erythropoietin in multiple body organs, including the brain, kidney and liver. In fact, the method disclosed herein even increases the content of endogenous erythropoietin in animals undergoing bilateral nephrectomy.

The method disclosed herein demonstrates that the content of erythropoietin can be increased even when the renal function is impaired. Although the present disclosure is not limited by the mechanism of erythropoietin production, the decrease in erythropoietin secretion that is typically seen during renal failure can be attributed to hyperoxia caused by increased flow/perfusion in renal tissue.

In another aspect, the methods disclosed herein increase levels of hematocrit and blood hemoglobin in an animal treated in vivo. As the increase in plasma EPO, hematocrit, and blood hemoglobin produced by the compounds used in the methods disclosed herein is dose sensitive, the dosage regimen can be determined to produce a constant, controlled level of responsiveness of the compounds disclosed herein. On the other hand, the treatment with the compounds disclosed herein can treat anemia, such as anaemia induced by toxic compounds such as chemotherapeutic agent cisplatin, or anemia due to blood loss, such as trauma, injury, parasite, or surgery.

In animals treated with the compounds disclosed herein, there is an increase in the percentage of circulating immature red blood cells (reticulocytes) in the blood before hematocrit and blood hemoglobin increase. Thus, the present disclosure encompasses the use of a compound of the present disclosure in a method of increasing the content of reticulocytes in the blood of an animal to produce an acellular reticulocyte lysate (as described by Pelham and Jackson in Eur. J. Biochem. 1976, 67, 247-256). By treating with the compound disclosed herein alone or in combination with another compound such as acetylphenylhydrazine or the like, the content of circulating reticulocytes in animals (e.g., rabbits, etc.) is increased.

Compared with the prior art, the beneficial effects of the present disclosure are that the compounds disclosed herein can be used to modulate hypoxia inducible factor (HIF) and/or endogenous erythropoietin (EPO). The metabolism of the compound in the organism is altered by deuteration techniques to give the compound better pharmacokinetic parameter characteristics. In this case, the dose can be changed and a long-acting formulation can be formed to improve the applicability. The use of deuterium to replace hydrogen atoms in the compound can increase the drug concentration of the compound in animals due to its deuterium isotope effect, so as to improve the efficacy of the drug. The replacement of hydrogen atoms in compounds with deuterium may increase the safety of the compounds due to the inhibition of certain metabolites.

DETAILED DESCRIPTION OF THE EMBODIMENTS

The method for preparing the compounds of Formula (I) according to the present disclosure will be more specifically described below, but these specific methods do not impose any limitations on the present disclosure. The compounds disclosed herein can also be conveniently prepared by combining various synthesis methods described in this specification or known in the art, and such combinations can be easily performed by those skilled in the art to which the present disclosure pertains.

In general, in a preparation process, each reaction is usually carried out in an inert solvent at room temperature to reflux temperature (e.g., 0° C. to 100° C., preferably 0° C. to 80° C.). The reaction time is usually 0.1 to 60 hours, preferably 0.5 to 24 hours.

Example 1: Preparation of N-[(4-hydroxy-1-methyl-7-phenoxy-3-isoquinolinyl)carbonyl]-2,2-d$_2$-glycine (Compound 11)

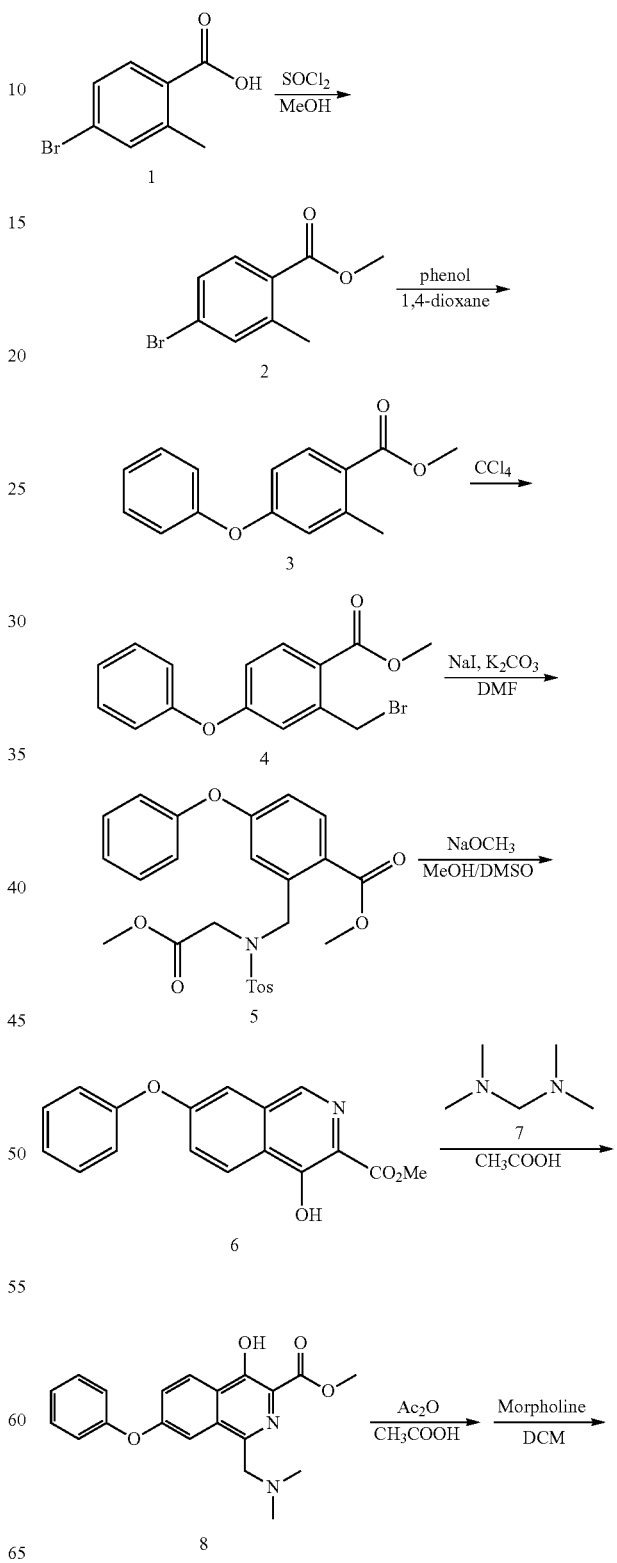

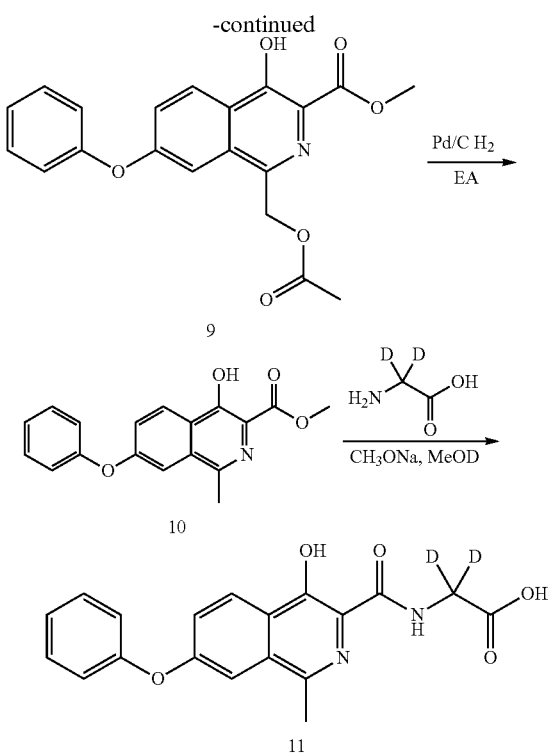

Step 1: Synthesis of methyl 4-bromo-2-methylbenzoate (Compound 2)

In an ice bath, thionyl chloride (5.50 mL, 70.00 mmol) was added dropwise to a solution of 4-bromo-2-methylbenzoic acid (5.00 g, 23.2 mmol) in methanol (60 mL). After the addition was complete, the reaction solution was stirred at reflux for 5 hours, cooled to room temperature and concentrated under reduced pressure. The concentrate was adjusted to neutral with saturated sodium bicarbonate solution, and extracted with ethyl acetate. The organic layer was washed with brine, dried over anhydrous sodium sulfate, and concentrated under reduced pressure to give 4.3 g of a light yellow oil. Yield: 81.1%. $^1$H NMR (300 MHz, CDCl$_3$) (δ/ppm) 7.79 (d, J=8.3 Hz, 1H), 7.45-7.35 (m, 2H), 3.89 (s, 3H), 2.58 (s, 3H).

Step 2: Synthesis of methyl 2-methyl-4-phenoxybenzoate (Compound 3)

Under nitrogen protection, 1,4-dioxane (30 mL) was added to a mixture of methyl 4-bromo-2-methylbenzoate (4.30 g, 18.80 mmol), phenol (1.90 g, 20.00 mmol), Cs$_2$CO$_3$ (18.40 g, 56.40 mmol), copper iodide (716 mg, 3.76 mmol) and N,N-dimethylglycine (775 mg, 7.52 mmol), and the reaction solution was stirred at 100° C. overnight, cooled to room temperature, filtered, and concentrated under reduced pressure. The concentrate was washed with ethyl acetate (100 mL) and water (60 mL). The organic layer was washed with brine, dried over anhydrous sodium sulfate, and concentrated under reduced pressure. The concentrate was subjected to column separation to obtain 3.60 g of a brown oil. Yield: 79.1%. $^1$H NMR (400 MHz, CDCl$_3$) (δ/ppm) 7.97-7.93 (m, 1H), 7.44-7.37 (m, 2H), 7.20 (dd, J=10.7, 4.2 Hz, 1H), 7.08 (dd, J=8.5, 0.9 Hz, 2H), 6.88-6.79 (m, 2H), 3.89 (s, 3H), 2.60 (s, 3H).

Step 3: Synthesis of methyl 2-(bromomethyl)-4-phenoxybenzoate (Compound 4)

Under nitrogen protection, benzoyl peroxide (BPO, 638 mg, 2.60 mmol) was added to a solution of methyl 2-methyl-4-phenoxybenzoate (9.10 g, 37.60 mmol) and N-bromosuccinimide (NBS, 7.02 g, 39.5 mmol) in carbon tetrachloride (160 mL). The reaction was stirred at reflux for 6 hours. The mixture was cooled to room temperature and filtered. The filtrate was washed with saturated aqueous sodium bicarbonate and brine, respectively, and dried over anhydrous sodium sulfate. The mixture was concentrated under reduced pressure, and the concentrate was subjected to column separation to obtain 10.9 g of a brown oil. Yield: 90.3%.

Step 4: Synthesis of methyl 2-(((N-(2-methoxy-2-oxoethyl)-4-methylphenyl)sulfonylamino) methyl)-4-phenoxybenzoate (Compound 5)

Sodium iodide (10.40 g, 69.50 mmol) and sodium carbonate (9.60 g, 69.50 mmol) were added to a solution of methyl 2-(bromomethyl)-4-phenoxybenzoate (14.90 mg, 46.00 mmol) and p-tosylglycine methyl ester (12.40 g, 51.00 mmol) in N,N-dimethylformamide (118 mL) at room temperature, and reacted at room temperature overnight. The reaction was quenched with water (100 mL) and extracted with ethyl acetate. The organic phase was washed respectively with water (100 mL) and brine (100 mL×2) and dried over anhydrous sodium sulfate. After concentration under reduced pressure, the concentrate was subjected to column separation to obtain 18.9 g of a brown oil. Yield: 85.0%. LC-MS (APCI): m/z=484.1 (M+1).

Step 5: Synthesis of methyl 4-hydroxy-7-phenoxyisoquinoline-3-carboxylate (Compound 6)

In an ice bath, a solution of sodium methoxide (12.70 g. 234.60 mmol) in methanol (40 mL) was added dropwise to a solution of methyl 2-(((N-(2-methoxy-2-oxoethyl)-4-methylphenyl)sulfonylamino)methyl)-4-phenoxybenzoate (18.90 g, 39.10 mmol) in dimethyl sulfoxide (82 mL). After completion of the addition, the reaction solution was stirred at room temperature for 2 hours. Methanol was removed under reduced pressure, the concentrate was diluted with water (50 mL), and the pH was adjusted to about pH 10 with 1N dilute hydrochloric acid. The mixture was extracted with ethyl acetate (100 mL×3), and the organic layer was washed with water (100 mL) and brine (100 mL), respectively, and dried over anhydrous sodium sulfate. After concentration under reduced pressure, the concentrate was subjected to column separation to obtain 9.1 g of a white solid. Yield: 78.8%. LC-MS (APCI): m/z=296.1 (M+1).

Step 6: Synthesis of methyl 1-((dimethylamino) methyl)-4-hydroxy-7-phenoxyisoquinoline-3-carboxylate (Compound 8)

At room temperature, N,N,N',N'-tetramethylmethylenediamine (1.08 g, 10.60 mmol) was slowly added dropwise to a solution of methyl 4-hydroxy-7-phenoxyisoquinoline-3-carboxylate (2.60 g, 8.80 mmol) in acetic acid (4 mL). The reaction was warmed to 55° C. and stirred for 6 hours. The mixture was cooled to room temperature and used directly for the next reaction. LC-MS (APCI): m/z=353.1 (M+1).

Step 7: Synthesis of methyl 1-((acetoxymethyl)methyl)-4-hydroxy-7-phenoxyisoquinolin-3-carboxylate (Compound 9)

Acetic anhydride (2.50 g, 24.60 mmol) was slowly added dropwise to the above reaction solution at room temperature while maintaining the temperature at 50° C. or lower. After the addition was completed, the reaction solution was heated to 100° C. and stirred overnight. After cooling to 60° C., 20 mL of water was slowly added, and then cooled to room temperature. The solid was filtered and the cake was washed with water. The filter cake was dissolved in 20 mL of dichloromethane and 10 mL of water, and stirred for 5 minutes, and the organic phase was separated. Morpholine (0.80 g, 8.80 mmol) was added to the organic phase in an ice bath and the reaction was stirred for 2 hours. The reaction mixture was concentrated under reduced pressure, mixed with acetone (2 mL) and methanol (2 mL), and the solid precipitated in an ice bath. The solid was filtered, washed with methanol (cold, 1 mL) and dried in vacuo to give 1.80 g of a white solid. Yield: 55.7%. LC-MS (APCI): m/z=367.1 (M+1).

Step 8: Synthesis of methyl 4-hydroxy-1-methyl-7-phenoxyisoquinoline-3-carboxylate (Compound 10)

methyl 1-((acetoxymethyl)methyl)-4-hydroxy-7-phenoxyisoquinolin-3-carboxylate (1.30 g, 3.50 mmol) was dissolved in anhydrous ethyl acetate (26 mL). Sodium carbonate (186 mg, 1.80 mmol) and Pd/C (10%, 170 mg) were added and the reaction solution was stirred under hydrogen at 80° C. overnight. After cooling to room temperature, the mixture was filtered through celite and the filtrate was concentrated under reduced pressure. The crude product was separated by column to give 600 mg of a white solid. Yield: 55.4%. LC-MS (APCI): m/z=310.1 (M+1).

Step 9: Synthesis of N-[(4-hydroxy-1-methyl-7-phenoxy-3-isoquinolinyl)carbonyl]-2,2-d$_2$-glycine (Compound 11)

Sodium methoxide (220 mg, 4.00 mmol) was added to a solution of methyl 4-hydroxy-1-methyl-7-phenoxyisoquinoline-3-carboxylate (120 mg, 0.39 mmol) and deuterated glycine-d$_5$ (100 mg, 1.20 mmol) in deuterated methanol-d$_4$ (3 mL) at room temperature, and the reaction solution was sealed in a tube to react at 110° C. overnight. The reaction solution was cooled to room temperature. The solid was filtered, washed with methanol (cold, 10 mL) and dried. The solid was dissolved in 5 mL of water and extracted with ethyl acetate (5 mL). The aqueous phase was adjusted to acidic pH with 0.5 mL of acetic acid, and the suspension was stirred at room temperature until a large amount of solid precipitated. The solid was filtered. The cake was washed with water (3×1 mL) and acetone (cold, 2×0.5 mL), and dried in vacuo to afford 60 mg of an off-white solid. Yield: 45.2%, LC-MS (APCI): m/z=355.2 (M+1); $^1$H NMR (300 MHz, DMSO-d$_6$) (δ/ppm) 13.32 (s, 1H), 12.80 (s, 1H), 9.10 (s, 1H), 8.29 (d, J=9.0 Hz, 1H), 7.61 (d, J=2.2 Hz, 1H), 7.50 (m, 3H), 7.25 (t, J=7.4 Hz, 1H), 7.17 (d, J=7.7 Hz, 2H), 2.70 (s, 3H).

Example 2: Preparation of N-[(4-hydroxy-1-d-methyl-7-phenoxy-3-isoquinolinyl)carbonyl] glycine (Compound 13)

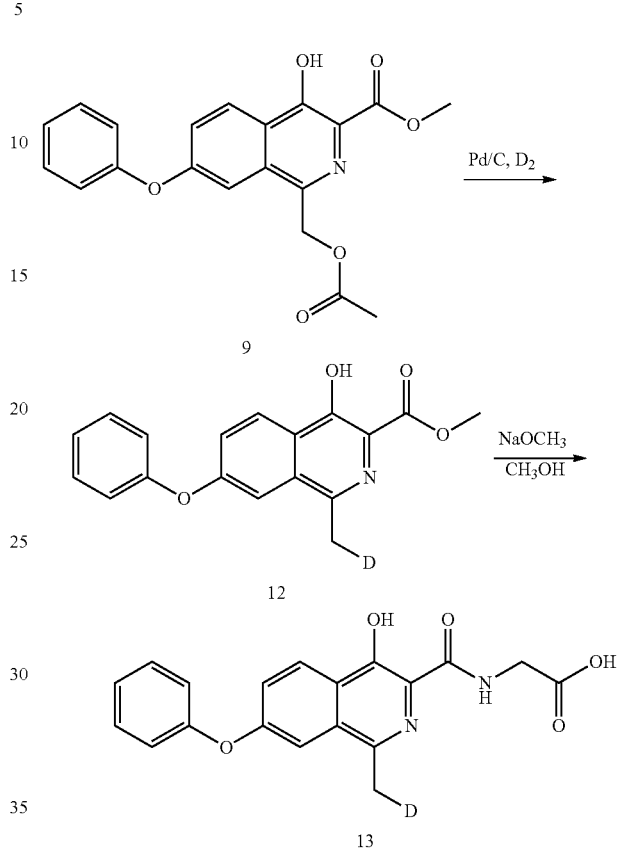

Step 1: Synthesis of methyl 4-hydroxy-1-(d-methyl)-7-phenoxyisoquinolin-3-carboxylate (Compound 12)

Methyl 1-((acetoxymethyl)methyl)-4-hydroxy-7-phenoxyisoquinolin-3-carboxylate (250 mg, 0.68 mmol) was dissolved in dry ethyl acetate (5 mL). Sodium carbonate (40 mg, 0.34 mmol) and Pd/C (50% in D$_2$O, 30 mg) were added and the reaction solution was stirred under hydrogen at 80° C. overnight. After cooling to room temperature, the mixture was filtered through celite and the filtrate was concentrated under reduced pressure. The crude product was separated by column to give 130 mg of a white solid. Yield: 61.6%. LC-MS (APCI): m/z=311.1 (M+1); $^1$H NMR (300 MHz, DMSO-d$_6$) (δ/ppm) 11.50 (s, 1H), 8.34 (m, 1H), 7.60 (d, J=2.1 Hz, 1H), 7.51 (m, 3H), 7.26 (t, J=7.4 Hz, 1H), 7.19 (m, 2H), 3.95 (s, 3H), 2.63 (d, J=5.3 Hz, 2H).

Step 2: Synthesis of N-[(4-hydroxy-1-(-d-methyl)-7-phenoxy-3-isoquinolinyl)carbonyl]glycine (Compound 13)

Sodium methoxide (226.8 mg, 4.20 mmol) was added to a solution of methyl 4-hydroxy-1-(methyl-d)-7-phenoxyisoquinolin-3-carboxylate (130 mg, 0.42 mmol) and glycine (94.5 mg, 1.30 mmol) in deuterated methanol (3 mL) at room temperature. The reaction solution was sealed in a tube to react at 110° C. overnight. The reaction was cooled to room temperature. The solid was filtered, washed with methanol (cold, 1 mL) and dried. The solid was dissolved in 3 mL of water and extracted with ethyl acetate (3 mL). The aqueous phase was adjusted to acidic pH with acetic acid, and the suspension was stirred at room temperature until a large amount of solid precipitated. The solid was filtered. The cake was washed respectively with water (3×1 mL) and acetone (cold, 2×0.5 mL) and dried in vacuo to give 29 mg of a white solid. Yield: 19.5%, LC-MS (APCI): m/z=354.1 (M+1); $^1$H NMR (300 MHz, DMSO-d$_6$) (δ/ppm) 13.32 (s, 1H), 12.79 (s, 1H), 9.11 (t, J=6.1 Hz, 1H), 8.30 (m, 1H)), 7.62 (d, J=2.0 Hz, 1H), 7.51 (m, 3H), 7.25 (t, J=7.3 Hz, 1H), 7.18 (d, J=7.8 Hz, 2H), 4.04 (d, J)=6.1 Hz, 2H), 2.69 (s, 2H).

Example 3: Preparation of N-[(4-hydroxy-1-methyl-7-(2,4,6-d$_3$-phenoxy))-3-isoquinolinyl) carbonyl] glycine (Compound 23)

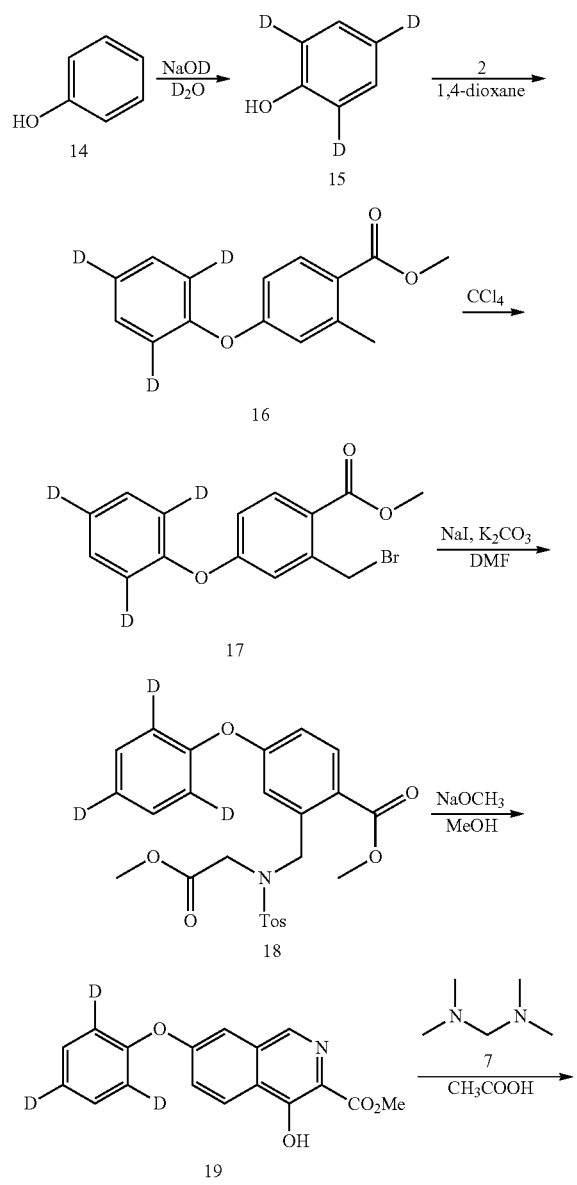

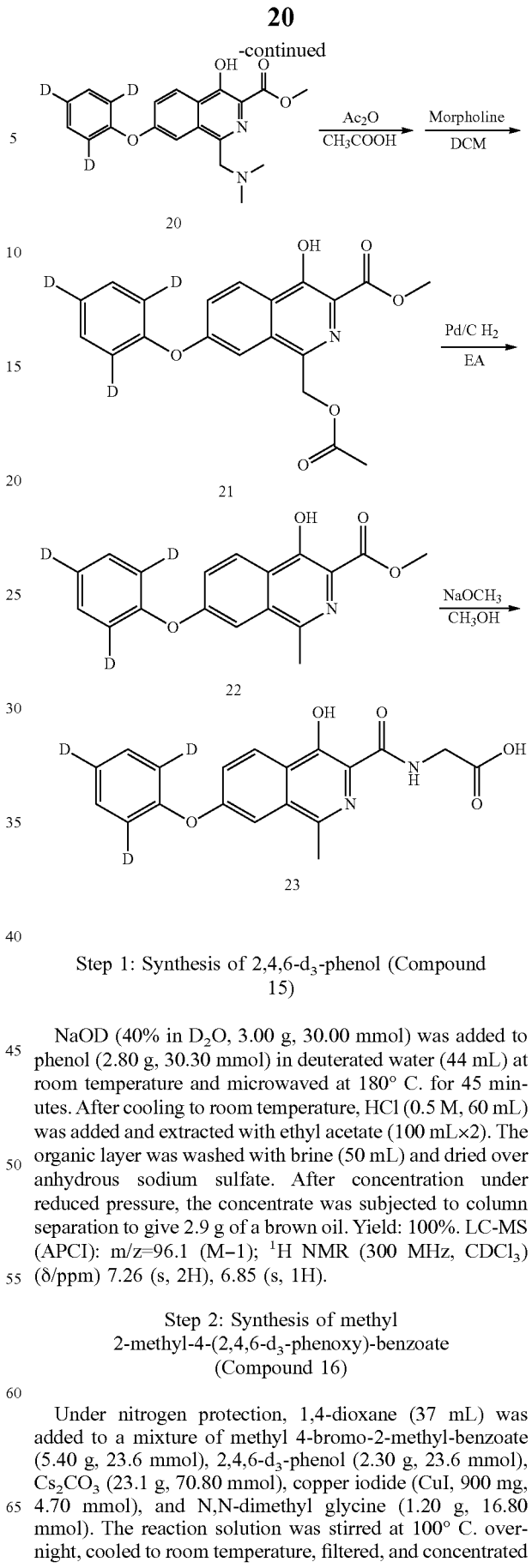

Step 1: Synthesis of 2,4,6-d$_3$-phenol (Compound 15)

NaOD (40% in D$_2$O, 3.00 g, 30.00 mmol) was added to phenol (2.80 g, 30.30 mmol) in deuterated water (44 mL) at room temperature and microwaved at 180° C. for 45 minutes. After cooling to room temperature, HCl (0.5 M, 60 mL) was added and extracted with ethyl acetate (100 mL×2). The organic layer was washed with brine (50 mL) and dried over anhydrous sodium sulfate. After concentration under reduced pressure, the concentrate was subjected to column separation to give 2.9 g of a brown oil. Yield: 100%. LC-MS (APCI): m/z=96.1 (M−1); $^1$H NMR (300 MHz, CDCl$_3$) (δ/ppm) 7.26 (s, 2H), 6.85 (s, 1H).

Step 2: Synthesis of methyl 2-methyl-4-(2,4,6-d$_3$-phenoxy)-benzoate (Compound 16)

Under nitrogen protection, 1,4-dioxane (37 mL) was added to a mixture of methyl 4-bromo-2-methyl-benzoate (5.40 g, 23.6 mmol), 2,4,6-d$_3$-phenol (2.30 g, 23.6 mmol), Cs$_2$CO$_3$ (23.1 g, 70.80 mmol), copper iodide (CuI, 900 mg, 4.70 mmol), and N,N-dimethyl glycine (1.20 g, 16.80 mmol). The reaction solution was stirred at 100° C. overnight, cooled to room temperature, filtered, and concentrated under reduced pressure. The concentrate was washed with ethyl acetate (100 mL) and water (60 mL), and the organic layer was washed with brine, dried over anhydrous sodium sulfate, and concentrated under reduced pressure. The concentrate was subjected to column separation to obtain 3.40 g of a brown oil. Yield: 58.7%.

Step 3: Synthesis of methyl 2-(bromomethyl)-4-(2, 4,6-$d_3$-phenoxy)-benzoate (Compound 17)

Under nitrogen protection, benzoyl peroxide (BPO, 170.8 mg, 0.70 mmol) was added to a solution of methyl 2-methyl-4-(2,4,6-$d_3$-phenoxy)-benzoate (3.40 g, 14.10 mmol) and N-bromosuccinimide (NBS, 2.38 g, 13.40 mmol) in carbon tetrachloride (58 mL), and stirred at reflux overnight. The mixture was cooled to room temperature and filtered. The filtrate was washed respectively with saturated aqueous sodium bicarbonate and brine, and dried over anhydrous sodium sulfate. After concentration under reduced pressure, the concentrate was subjected to column separation to obtain 2.90 g of a brown oil. Yield: 63.5%.

Step 4: Synthesis of methyl 2-(((N-(2-methoxy-2-oxoethyl)-4-methylphenyl)sulfonylamino) methyl)-4-(2,4,6-$d_3$-phenoxy)-benzoate (compound 18)

Sodium iodide (2.00 g, 13.40 mmol) and potassium carbonate (1.85 g, 13.40 mmol) was added to methyl 2-(bromomethyl)-4-(2,4,6-$d_3$-phenoxy)-benzoate (2.90 g, 8.95 mmol) and p-toluenesulfonyl glycine methyl ester (2.40 g, 9.85 mmol) in N,N-dimethylformamide (23 mL) at room temperature, and reacted at room temperature for 6 hours. The reaction was quenched with water (50 mL) and extracted with ethyl acetate (50 mL×3). The organic phase was respectively washed with water (50 mL) and brine (50 mL×2) and dried over anhydrous sodium sulfate. The mixture was concentrated under reduced pressure, and the concentrate was subjected to column separation to obtain 4.20 g of a yellow solid. Yield: 96.4%. LC-MS (APCI): m/z=487.1 (M+1).

Step 5: Synthesis of methyl 4-hydroxy-7-(2,4,6-$d_3$-phenoxy)-isoquinolin-3-carboxylate (Compound 19)

In an ice bath, a solution of sodium methoxide (3.02 g, 55.90 mmol) in methanol-d (9 mL) was added dropwise to a solution of methyl 2-(((N-(2-methoxy-2-oxoethyl)-4-methylphenyl)sulfonylamino)methyl)-4-(2,4,6-$d_3$-phenoxy)-benzoate (4.20 g, 8.60 mmol) in dimethyl sulfoxide (18 mL). After the addition was completed, the reaction solution was stirred at room temperature for 2 hours. Methanol was removed under reduced pressure, the concentrate was diluted with water (50 mL), and the pH was adjusted to about pH 10 with 1N dilute hydrochloric acid. The mixture was extracted with ethyl acetate (50 mL×3), and the organic layer was washed with water (50 mL) and brine (50 mL), respectively, and dried over anhydrous sodium sulfate. After concentration under reduced pressure, the concentrate was separated by column to give 2.50 g of a white solid. Yield: 96.6%. LC-MS (APCI): m/z=299.1 (M+1).

Step 6: Synthesis of methyl 1-((dimethylamino) methyl)-4-hydroxy-7-(2,4,6-$d_3$-phenoxy)-quinolin-3-carboxylate (Compound 20)

At room temperature, N,N,N',N'-tetramethylmethylenediamine (830 mg, 7.80 mmol) was slowly added dropwise to a solution of methyl 4-hydroxy-7-(2,4,6-$d_3$-phenoxy)-isoquinolin-3-carboxylate (2.00 g, 6.70 mmol) in acetic acid (4 mL). The reaction was warmed to 55° C. and stirred for 6 hours. The mixture was cooled to room temperature and used directly for the next reaction. LC-MS (APCI): m/z=356.2 (M+1).

Step 7: Synthesis of methyl 1-((acetoxymethyl) methyl)-4-hydroxy-7-((2,4,6-$d_3$-phenoxy)-isoquinolin-3-carboxylate (Compound 21)

Acetic anhydride (1.80 g, 16.50 mmol) was slowly added dropwise to the above reaction at room temperature while maintaining the temperature at 50° C. or lower. After the addition was completed, the reaction solution was heated to 100° C. and stirred overnight. After cooling to 60° C., 25 mL of water was slowly added, and the temperature was lowered to room temperature. The solid was filtered and the cake was washed with water. The filter cake was dissolved in 25 mL of dichloromethane and 12 mL of water, stirred for 5 minutes, and the organic phase was separated. Morpholine (0.90 g) was added to the organic phase in an ice bath and stirred for 2 hours. The reaction mixture was concentrated under reduced pressure, mixed with acetone (2 mL) and methanol (2 mL), and the solid precipitated in an ice bath. The solid was filtered, washed with methanol (cold, 1 mL) and dried in vacuo to give 1.20 g of a white solid. Yield: 55.9. %. LC-MS (APCI): m/z=370.1 (M+1).

Step 8: Synthesis of methyl 4-hydroxy-1-methyl-7-(2,4,6-$d_3$-phenoxy)-isoquinolin-3-carboxylate (Compound 22)

Methyl 1-((acetoxymethyl)methyl)-4-hydroxy-7-(phenyl-2,4,6-$d_3$-oxy)-isoquinolin-3-carboxylate (300 mg, 0.81 mmol) was dissolved in anhydrous ethyl acetate (6 mL). Sodium carbonate (53 mg, 0.40 mmol) and Pd/C (10%, 45 mg) were added, and the reaction was stirred under hydrogen at 80° C. overnight. After cooling to room temperature, the mixture was filtered through celite and the filtrate was concentrated under reduced pressure. The crude product was separated by column to give 220 mg of a white solid. Yield: 86.90%. LC-MS (APCI): m/z=313.1 (M+1).

Step 9: Synthesis of N-[(4-hydroxy-1-methyl-7-(2, 4,6-$d_3$-phenoxy)-3-(3-isoquinolinyl) carbonyl]glycine (Compound 23)

Sodium methoxide (383.8 g, 7.10 mmol) was added to a solution of methyl 4-hydroxy-1-methyl-7-(2,4,6-$d_3$-phenoxy)-isoquinolin-3-carboxylate (220 mg, 0.70 mmol) and deuterated glycine-$d_5$ (169.2 mg, 2.12 mmol) in deuterated methanol-d (4.8 mL) at room temperature and sealed in a tube to react at 110° C. overnight. The reaction was cooled to room temperature. The solid was filtered, washed with methanol (cold, 3 mL) and dried. The solid was dissolved in 3 mL of water and extracted with ethyl acetate (3 mL). The aqueous phase was adjusted to acidic pH with acetic acid, and the suspension was stirred at room temperature until a large amount of solid precipitated. The solid was filtered. The cake was washed respectively with water (3×2 mL) and acetone (cold, 2×2 mL) and dried in vacuo to give 126 mg of a white solid. Yield: 49.7%, LC-MS (APCI): m/z=356.2 (M+1); $^1$H NMR (300 MHz, DMSO-$d_6$) (δ/ppm) 13.34 (s, 1H), 9.07 (s, 1H), 8.29 (d, J=9.0 Hz, 1H), 7.62 (d, J=2.3 Hz, 1H), 7.53 (dd, J=9.0, 2.4 Hz, 1H), 7.48 (d, J=4.0 Hz, 2H), 4.04 (d, J=6.1 Hz, 2H), 2.70 (s, 3H).

Example 4: Preparation of N-[(4-hydroxy-1-methyl-7-(d$_5$-phenoxy)-3-isoquinolinyl) carbonyl] glycine

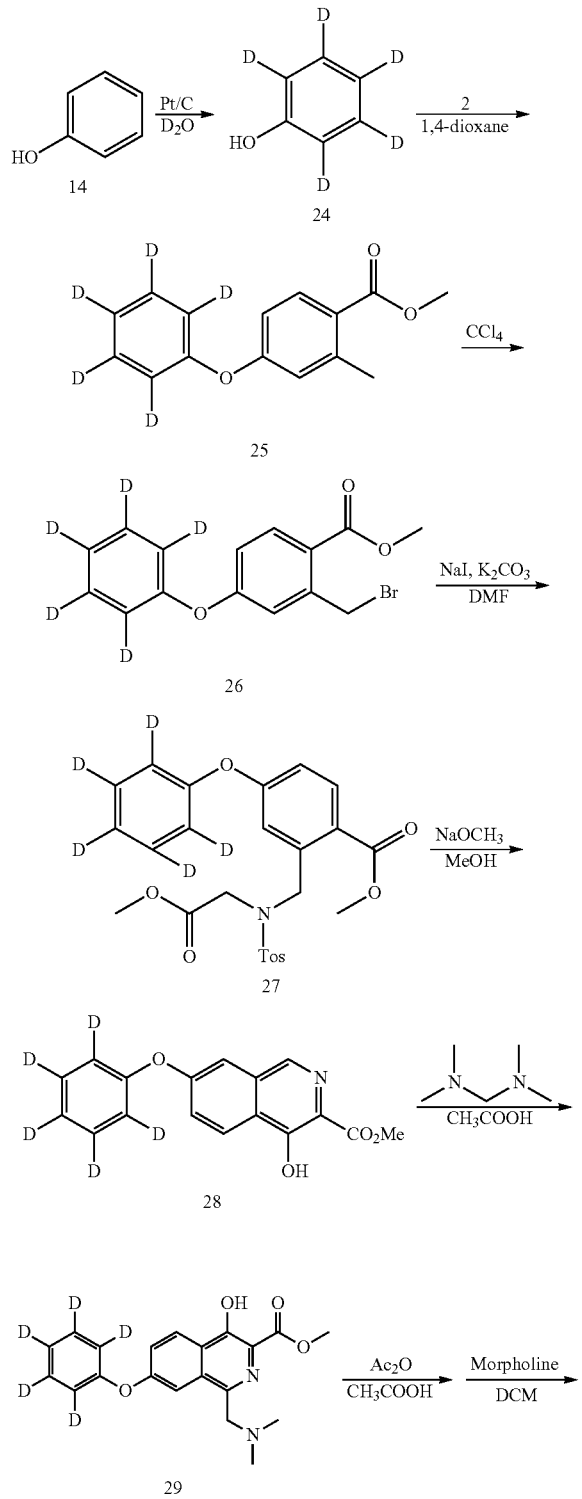

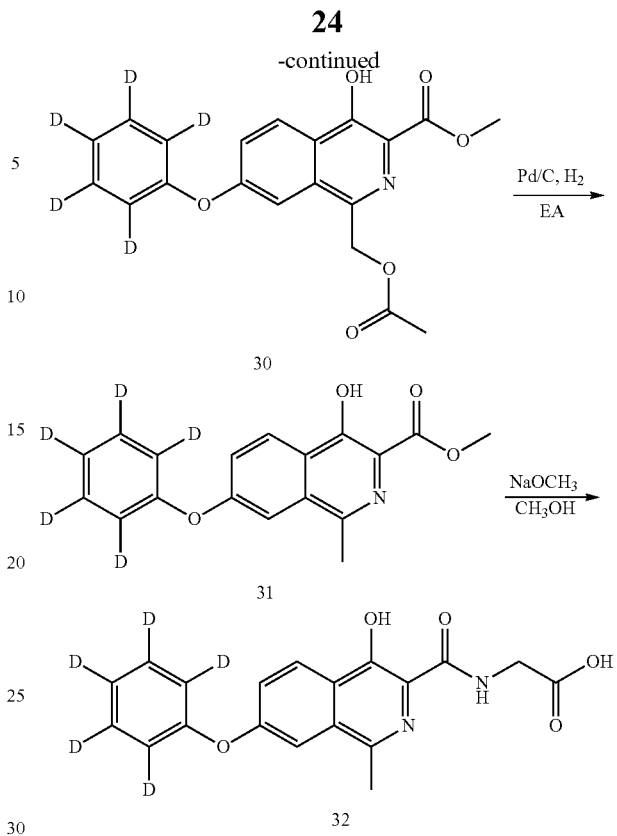

Step 1: Synthesis of d$_5$-phenol (Compound 24)

5% Pt/C (600 mg) was added to phenol (3.00 g, 31.90 mmol) in heavy water (100 mL) at room temperature. H$_2$ was used to displace the air of the reaction system and the reaction was sealed in a tube to react at room temperature for 48 hours. The mixture was filtered through celite, and the filtrate was extracted with ethyl acetate (100 mL). The organic layer was washed with brine and dried over anhydrous sodium sulfate. Concentration under reduced pressure gave 3.0 g of a brown oil which was used in the next step without purification. LC-MS (APCI): m/z=98.1 (M−1).

Step 2: Synthesis of methyl 2-methyl-4-(d$_5$-phenoxy)-benzoate (Compound 25)

Under nitrogen protection, 1,4-dioxane (50 mL) was added to a mixture of methyl 4-bromo-2-methyl-benzoate (7.60 g, 33.3 mmol), d$_5$-phenol (3.00 g, 30.3 mmol), Cs$_2$CO$_3$ (29.60 g, 100 mmol), copper iodide (1.30 g, 6.66 mmol), and N,N-dimethyl glycine (1.70 g, 16.50 mmol) and the reaction was stirred at 100° C. overnight. The mixture was cooled to room temperature, filtered, and concentrated under reduced pressure. The concentrate was washed with ethyl acetate (100 mL) and water (60 mL), and the organic layer was washed with brine, dried over anhydrous sodium sulfate, and concentrated under reduced pressure. The concentrate was subjected to column separation to obtain 4.30 g of a brown oil. Yield: 68.7%.

Step 3: Synthesis of methyl 2-(bromomethyl)-4-(d$_5$-phenoxy)-benzoate (Compound 26)

Under nitrogen protection, benzoyl peroxide (BPO, 296 mg, 1.23 mmol) was added to a solution of methyl 2-methyl- 4-($d_5$-phenoxy)-benzoate (4.30 g, 17.50 mmol) and N-bromide succinimide (NBS, 3.27 g, 18.30 mmol) in carbon tetrachloride (75 mL) and stirred at reflux overnight. The mixture was cooled to room temperature and filtered. The filtrate was washed respectively with saturated aqueous sodium bicarbonate and brine, and dried over anhydrous sodium sulfate. The mixture was concentrated under reduced pressure, and the concentrate was subjected to column separation to obtain 4.10 g of a brown oil. Yield: 71.8%.

Step 4: Synthesis of methyl 2-(((N-(2-methoxy-2-oxoethyl)-4-methylphenyl)sulfonylamino) methyl)-4-($d_5$-phenoxy)-benzoate (Compound 27)

Sodium iodide (2.80 g, 18.90 mmol) and potassium carbonate (2.60 g, 18.90 mmol) was added to methyl 2-(bromomethyl)-4-($d_5$-phenoxy)-benzoate (4.10 g, 12.60 mmol) and p-toluenesulfonyl glycine methyl ester (3.37 g, 13.90 mmol) in N,N-dimethylformamide (35 mL) at room temperature. The reaction was allowed to react at room temperature overnight. The reaction was quenched with water (50 mL) and extracted with ethyl acetate (50 mL×3). The organic phase was washed respectively with water (50 mL) and brine (50 mL×2) and dried over anhydrous sodium sulfate. The mixture was concentrated under reduced pressure, and the concentrate was subjected to column separation to give 5.4 g of a yellow solid. Yield: 87.7%. LC-MS (APCI): m/z=489.1 (M+1).

Step 5: Synthesis of methyl 4-hydroxy-7-($d_5$-phenoxy)-isoquinolin-3-carboxylate (Compound 28)

In an ice bath, a solution of sodium methoxide (3.90 g. 71.90 mmol) in methanol (11 mL) was added dropwise to a solution of methyl 2-2-(((N-(2-methoxy-2-oxoethyl)-4-methylphenyl)sulfonylamino)methyl)-4-($d_5$-phenoxy)-benzoate (5.40 g, 11.1 mmol) in dimethyl sulfoxide (23 mL). After the addition was completed, the solution was stirred at room temperature for 2 hours. Methanol was removed under reduced pressure, the concentrate was diluted with water (50 mL), and the pH was adjusted to about pH 10 with 1N dilute hydrochloric acid. The mixture was extracted with ethyl acetate (50 mL×3), and the organic layer was washed with water (50 mL) and brine (50 mL), respectively, and dried over anhydrous sodium sulfate. After concentration under reduced pressure, the concentrate was separated by column to give 3.00 g of a white solid. Yield: 90.2%. LC-MS (APCI): m/z=301.1 (M+1).

Step 6: Synthesis of methyl 1-((dimethylamino)methyl)-4-hydroxy-7-($d_5$-phenoxy)-isoquinolin-3-carboxylate (Compound 29)

At room temperature, N,N,N',N'-tetramethylmethylenediamine (1.23 g, 12.00 mmol) was slowly added dropwise to a solution of methyl 4-hydroxy-7-($d_5$-phenoxy)-isoquinolin-3-carboxylate (3.00 g, 10.00 mmol) in acetic acid (5 mL), the reaction was warmed to 55° C. and the reaction solution was stirred for 6 hours. The mixture was cooled to room temperature and used directly for the next reaction. LC-MS (APCI): m/z=358.1 (M+1).

Step 7: Synthesis of methyl 1-((acetoxymethyl)methyl)-4-hydroxy-7-($d_5$-phenoxy)-isoquinolin-3-carboxylate (Compound 30)

Acetic anhydride (2.50 g, 24.60 mmol) was slowly added dropwise to the above reaction at room temperature while maintaining the temperature at 50° C. or lower. After the addition was completed, the reaction solution was heated to 100° C. and stirred overnight. After cooling to 60° C., 25 mL of water was slowly added, and the temperature was lowered to room temperature. The solid was filtered and the filter cake was washed with water. The cake was dissolved in 25 mL of dichloromethane and 12 mL of water, stirred for 5 minutes, and the organic phase was separated. Morpholine (0.90 g) was added to the organic phase in an ice bath and the reaction was stirred for 2 hours. The reaction solution was concentrated under reduced pressure, mixed with acetone (2 mL) and methanol (2 mL), and the solid precipitated in an ice bath. The solid was filtered, washed with methanol (cold, 1 mL) and dried under vacuum to give 2.08 g of a white solid. Yield: 55.9%. LC-MS (APCI): m/z=372.1 (M+1).

Step 8: Synthesis of methyl 4-hydroxy-1-methyl-7-(phenyl-$d_5$-oxy)-isoquinolin-3-carboxylate (Compound 31)

Methyl 1-((acetoxymethyl)methyl)-4-hydroxy-7-($d_5$-phenoxy)-isoquinolin-3-carboxylate (500 mg, 1.34 mmol) was dissolved in anhydrous ethyl acetate (10 mL), sodium carbonate (75 mg, 0.70 mmol) and Pd/C (10%, 75 mg) were added and the reaction was stirred under hydrogen at 80° C. overnight. After cooling to room temperature, the mixture was filtered through celite and the filtrate was concentrated under reduced pressure. Column chromatography of the crude product gave 400 mg of a white solid. Yield: 94.70%. LC-MS (APCI): m/z=315.1 (M+1).

Step 9: Synthesis of N-[(4-hydroxy-1-methyl-7-($d_5$-phenoxy)-3-isoquinolinyl)carbonyl] glycine (Compound 32)

Sodium methoxide (1.05 g, 19.4 mmol) was added to a solution of methyl 4-hydroxy-1-methyl-7-($d_5$-phenoxy)-isoquinolin-3-carboxylate (200 mg, 0.64 mmol) and deuterated glycine-$d_5$ (154 mg, 1.92 mmol) in deuterated methanol-d (4.5 mL) at room temperature, and the reaction solution was sealed in a tube to react at 110° C. overnight. The reaction was cooled to room temperature. The solid was filtered, washed with methanol (cold, 5 mL) and dried. The solid was dissolved in 5 mL of water and extracted with ethyl acetate (5 mL). The aqueous phase was adjusted to acidic pH with acetic acid, and the suspension was stirred at room temperature until a large amount of solid precipitated. The solid was filtered. The cake was washed respectively with water (3×2 mL) and acetone (cold, 2×2 mL) and dried in vacuo to give 150 mg of a white solid. Yield: 65.2%. LC-MS (APCI): m/z=358.1 (M+1); $^1$H NMR (300 MHz, DMSO-$d_6$) (δ/ppm) 13.33 (s, 1H), 12.88 (s, 1H), 9.08 (s, 1H), 8.29 (d, J=9.0 Hz, 1H), 7.61 (d, J=2.0 Hz, 1H), 7.52 (dd, J=9.0, 2.2 Hz, 1H), 4.04 (d, J=6.1 Hz, 2H), 2.70 (s, 3H).

Example 5: Preparation of N-[(4-hydroxy-1-(d-methyl)-7-phenoxy-3-isoquinolinyl) carbonyl]-2,2-d₂-glycine

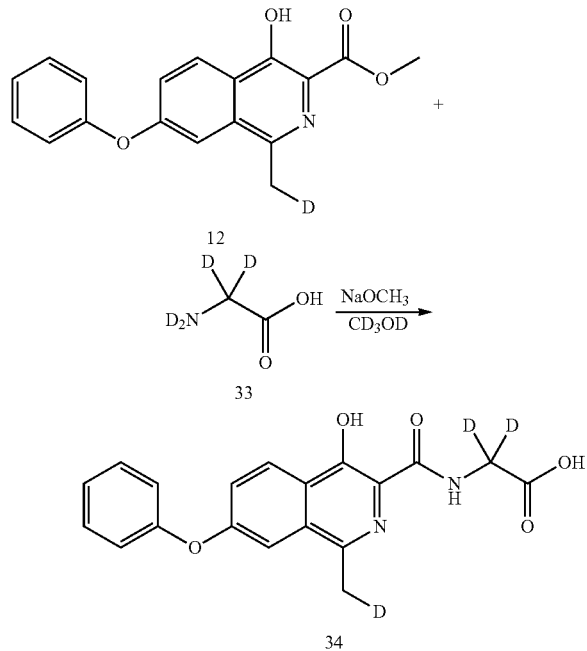

Sodium methoxide (243 mg, 4.5 mmol) was added to a solution of methyl 4-hydroxy-1-(d-methyl)-7-phenoxyisoquinolin-3-carboxylate (130 mg, 0.42 mmol) and deuterated d₅-glycine (108 mg, 1.35 mmol) in deuterated methanol-d (3 mL) at room temperature, and the reaction solution was sealed in a tube to react at 110° C. overnight. The reaction solution was cooled to room temperature. The solid was filtered, washed with methanol (cold, 1 mL) and dried. The solid was dissolved in 3 mL of water and extracted with ethyl acetate (3 mL). The aqueous phase was adjusted to acidic pH with acetic acid, and the suspension was stirred at room temperature until a large amount of solid precipitated. The solid was filtered. The cake was washed respectively with water (3×1 mL) and acetone (cold, 2×0.5 mL) and dried in vacuo to give 66 mg of an off-white solid. Yield: 41.2%, LC-MS (APCI): m/z=356.2 (M+1); ¹H NMR (300 MHz, DMSO-d₆) (δ/ppm) 13.35 (s, 1H), 9.07 (s, 1H), 8.29 (m, 1H), 7.62 (d, J=1.9 Hz, 1H), 7.51 (m, 3H), 7.25 (t, J=7.4 Hz, 1H), 7.17 (d, J=7.7 Hz, 2H), 2.69 (d, J=5.2 Hz, 2H).

Example 6: Preparation of N-[(4-hydroxy-1-(d₃-methyl)-7-phenoxy-3-isoquinolinyl) carbonyl]-2,2-d₂-glycine (Compound 36)

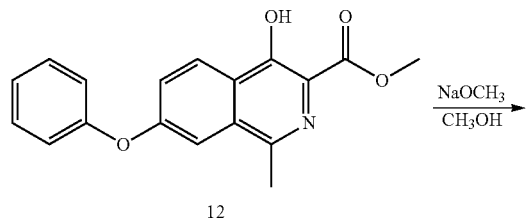

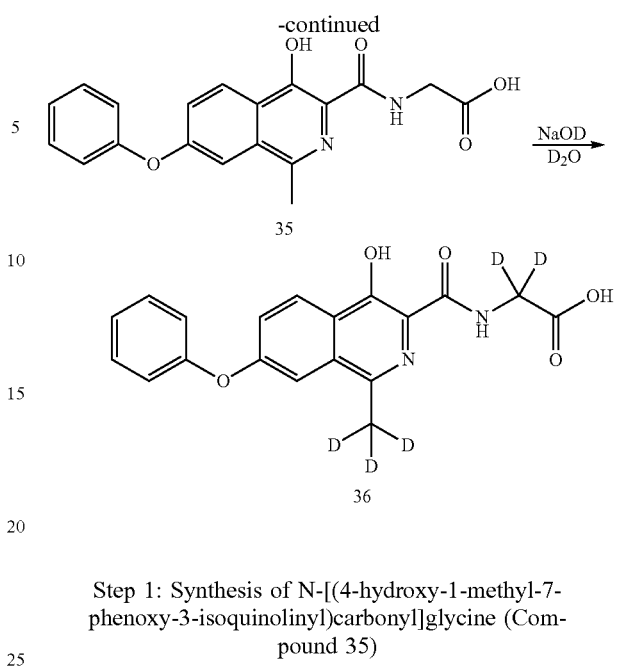

Step 1: Synthesis of N-[(4-hydroxy-1-methyl-7-phenoxy-3-isoquinolinyl)carbonyl]glycine (Compound 35)

Sodium methoxide (1.05 g, 19.4 mmol) was added to a solution of methyl 4-hydroxy-1-methyl-7-phenoxyisoquinolin-3-carboxylate (600 mg, 1.94 mmol) and glycine (437 mg, 5.80 mmol) in methanol (4 mL) at room temperature. The reaction solution was sealed in a tube to react at 110° C. overnight. The reaction was cooled to room temperature. The solid was filtered, washed with methanol (cold, 5 mL) and dried. The solid was dissolved in 5 mL of water and extracted with ethyl acetate (5 mL). The aqueous phase was adjusted to acidic pH with acetic acid, and the suspension was stirred at room temperature until a large amount of solid precipitated. The solid was filtered. The cake was washed respectively with water (3×2 mL) and acetone (cold, 2×2 mL) and dried in vacuo to give 125 mg of a white solid. Yield: 18.3%, LC-MS (APCI): m/z=353.1 (M+1); ¹H NMR (500 MHz, DMSO-d₆) (δ/ppm) 13.31 (s, 1H), 9.09 (s, 1H), 8.29 (d, J=9.0 Hz, 1H), 7.61 (d, J=2.2 Hz, 1H), 7.53 (dd, J=9.0, 2.2 Hz, 1H), 7.47 (t, J=7.9 Hz, 2H), 7.25 (t, J=7.4 Hz, 1H), 7.17 (d, J=7.9 Hz, 2H), 4.03 (d, J=6.1 Hz, 2H), 2.70 (s, 3H).

Step 2: Synthesis of the compound N-[(4-hydroxy-1-(d₃-methyl)-7-phenoxy-3-isoquinolinyl) carbonyl]-2,2-d₂-glycine (Compound 36)

A 40% solution of sodium deuteroxide in heavy water (0.20 mL) was added to N-[(4-hydroxy-1-methyl-7-phenoxy-3-isoquinolinyl)carbonyl]glycine (100 mg, 0.25 mmol) in heavy water (3 mL). The mixture was sealed in a tube under nitrogen protection and reacted at 140° C. for 8 hours. After cooling to room temperature, the system was adjusted to about pH 4 with 3N hydrochloric acid solution, and extracted with ethyl acetate (20 mL×4). The organic phase was washed with brine (15 mL), dried over anhydrous sodium sulfate, and concentrated under reduced pressure. The concentrate was subjected to preparative thin layer chromatography to give 15 mg of a gray solid. Yield: 30.0%, LC-MS (APCI): m/z=358.2 (M+1); ¹H NMR (300 MHz, DMSO-d₆) (δ/ppm) 13.43 (s, 1H), 9.01 (s, 1H), 8.30 (d, J=9.0 Hz, 1H), 7.62 (d, J=2.2 Hz, 1H), 7.52 (m, 3H), 7.26 (t, J=7.4 Hz, 1H), 7.18 (d, J=7.7 Hz, 2H).

Example 7: Preparation of N-[(4-hydroxy-1-methyl-7-(3-d-phenoxy)-3-isoquinolinyl) carbonyl]glycine (Compound 46)

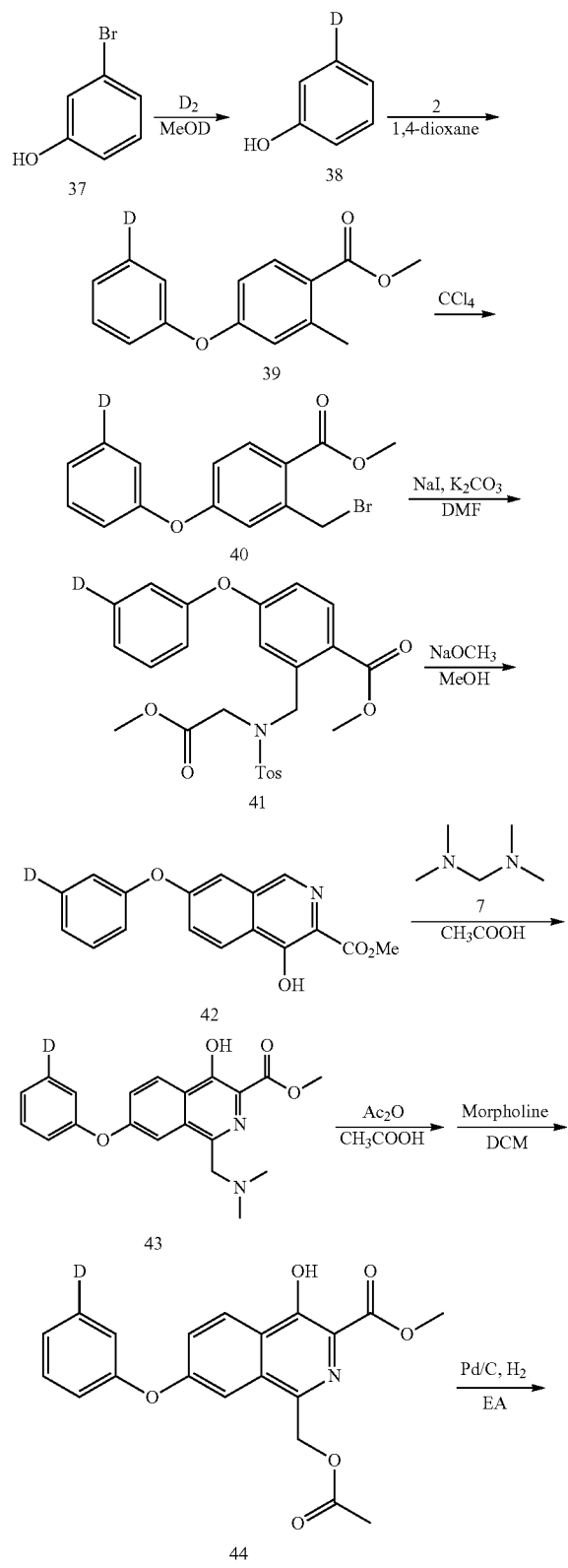

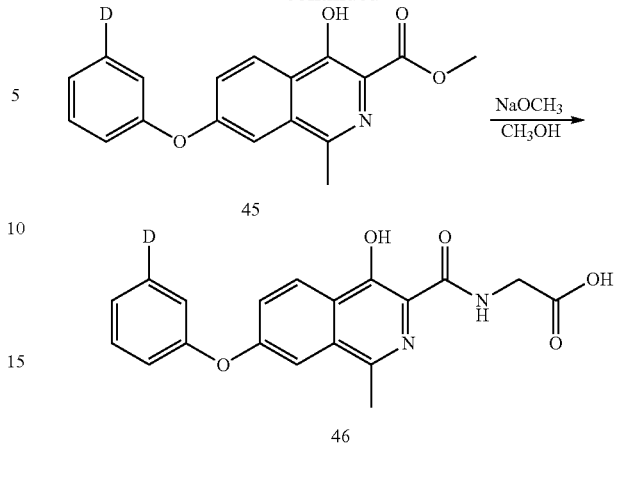

Step 1: Synthesis of 3-d-phenol (Compound 38)

Pd/C (50% in $D_2O$, 1.00 g) was added to m-bromophenol (3.50 g, 20.00 mmol) in deuterated methanol-d (20 mL) at room temperature. Air was replaced with $D_2$, and the mixture was reacted under a balloon of deuterium gas overnight. The mixture was filtered through celite. The filtrate was concentrated under reduced pressure, and the concentrate was subjected to column separation to obtain 2.8 g of a brown oil. Yield: 52.0%, LC-MS (APCI): m/z=94.1 (M−1); $^1$H NMR (300 MHz, $CDCl_3$) (δ/ppm) 7.26 (s, 2H), 6.85 (s, 1H).

Step 2: Synthesis of methyl 2-methyl-4-(3-d-phenoxy)-benzoate (Compound 39)

Under nitrogen protection, 1,4-dioxane (35 mL) was added to a mixture of methyl 4-bromo-2-methyl-benzoate (4.50 g, 19.80 mmol), 3-d-phenol (1.80 g, 18.90 mmol), $Cs_2CO_3$ (19.40 g, 59.4 mmol), copper iodide (754 mg, 3.96 mmol), and N,N-dimethyl glycine (815 mg, 7.90 mmol), and the reaction was stirred at 100° C. overnight. The mixture was cooled to room temperature, filtered, and concentrated under reduced pressure. The concentrate was washed with ethyl acetate (100 mL) and water (60 mL). The organic layer was washed with brine, dried over anhydrous sodium sulfate, and concentrated under reduced pressure. The concentrate was subjected to column separation to give 2.44 g of a brown oil. Yield: 58.9%.

Step 3: Synthesis of methyl 2-(bromomethyl)-4-(3-d-phenoxy)-benzoate (Compound 40)

Under nitrogen protection, benzoyl peroxide (BPO, 170.8 mg, 0.70 mmol) was added to a solution of methyl 2-methyl-4-(3-d-phenoxy)-benzoate (2.40 g, 10.00 mmol) and N-bromosuccinimide (NBS, 1.87 g, 10.5 mmol) in carbon tetrachloride (43 mL), and the reaction was stirred at reflux overnight. The mixture was cooled to room temperature and filtered. The filtrate was respectively washed with saturated aqueous sodium bicarbonate and brine, and dried over anhydrous sodium sulfate. The mixture was concentrated under reduced pressure and the concentrate was subjected to column separation to give 2.00 g of a brown oil. Yield: 62.1%.

Step 4: Synthesis of methyl 2-(((N-(2-methoxy-2-oxoethyl)-4-methylphenyl)sulfonylamino) methyl)-4-(3-d-phenoxy)benzoate (Compound 41)

Sodium iodide (1.39 g, 9.30 mmol) and potassium carbonate (1.28 g, 9.30 mmol) was added to methyl 2-(bromomethyl)-4-(3-d-phenoxy)-benzoate (2.00 g, 6.20 mmol) and p-toluenesulfonyl glycine methyl ester (1.66 g, 6.80 mmol) in N,N-dimethylformamide (16 mL) at room temperature, and reacted at room temperature for 4 hours. The reaction was quenched with water (50 mL) and extracted with ethyl acetate (50 mL×3). The organic phase was washed respectively with water (50 mL) and brine (50 mL×2) and dried over anhydrous sodium sulfate. Concentration under reduced pressure afforded 3.70 g of a yellow solid which was used in the next reaction without purification. Yield: 100%. LC-MS (APCI): m/z=485.1 (M+1).

Step 5: Synthesis of methyl 4-hydroxy-7-(3-d-phenoxy)-isoquinolin-3-carboxylate (Compound 42)

In an ice bath, a solution of sodium methoxide (4.10 g. 76.00 mmol) in methanol-d (8 mL) was added dropwise to a solution of methyl 2-(((N-(2-methoxy-2-oxoethyl)-4-methylphenyl)sulfonylamino)methyl)-4-(3-d-phenoxy)-benzoate (3.70 g, 7.60 mmol) in dimethyl sulfoxide (16 mL). After the addition was completed, the reaction was stirred at room temperature for 1 hour. Methanol was removed under reduced pressure, the concentrate was diluted with water (50 mL), and the pH was adjusted to about pH 10 with 1N dilute hydrochloric acid. The mixture was extracted with ethyl acetate (50 mL×3), and the organic layer was washed with water (50 mL) and brine (50 mL), respectively, and dried over anhydrous sodium sulfate. The mixture was concentrated under reduced pressure, and the concentrate was separated by column to give 1.10 g of a white solid. Yield over two steps: 59.9%. LC-MS (APCI): m/z=297.1 (M+1).

Step 6: Synthesis of methyl 1-((dimethylamino) methyl)-4-hydroxy-7-(3-d-phenoxy)-quinolin-3-carboxylate (Compound 43)

N,N,N',N'-tetramethylmethylenediamine (460 mg, 4.50 mmol) was slowly added dropwise to a solution of methyl 4-hydroxy-7-(3-d-phenoxy)-isoquinolin-3-carboxylate (1.10 g, 3.70 mmol) in acetic acid (2 mL) at room temperature, and the reaction was warmed to 55° C. and stirred for 6 hours. The mixture was cooled to room temperature and used directly for the next reaction. LC-MS (APCI): m/z=354.2 (M+1).

Step 7: Synthesis of methyl 1-((acetoxymethyl) methyl)-4-hydroxy-7-(3-d-phenoxy)-isoquinolin-3-carboxylate (Compound 44)

Acetic anhydride (1.10 g, 10.4 mmol) was slowly added dropwise to the above reaction at room temperature while maintaining the temperature at 50° C. or lower. After the addition was completed, the reaction solution was heated to 100° C. and stirred overnight. After cooling to 60° C., 10 mL of water was slowly added, and the temperature was lowered to room temperature. The solid was filtered and the filter cake was washed with water. The cake was dissolved in 10 mL of dichloromethane and 5 mL of water, stirred for 5 minutes, and the organic phase was separated. Morpholine (322 mg, 3.70 mmol) was added to the organic phase in an ice bath and the reaction was stirred for 2 hours. The reaction mixture was concentrated under reduced pressure, mixed with acetone (1 mL) and methanol (1 mL), and the solid precipitated in an ice bath. The solid was filtered, washed with methanol (cold, 1 mL) and dried in vacuo to give 920 mg of a white solid. Yield: 67.6%. LC-MS (APCI): m/z=368.1 (M+1).

Step 8: Synthesis of methyl 4-hydroxy-1-methyl-7-(3-d-phenoxy)-isoquinolin-3-carboxylate (Compound 45)

Methyl 1-((acetoxymethyl)methyl)-4-hydroxy-7-(3-d-phenoxy)-isoquinolin-3-carboxylate (920 mg, 2.50 mmol) was dissolved in anhydrous ethyl acetate (18 mL). Sodium carbonate (132 mg, 1.25 mmol) and Pd/C (10%, 140 mg) were added and the reaction was stirred under hydrogen at 80° C. overnight. After cooling to room temperature, the mixture was filtered through celite and the filtrate was concentrated under reduced pressure. The crude product was subjected to column separation to give 570 mg of a white solid. Yield: 73.50%. LC-MS (APCI): m/z=: 311.1 (M+1).

Step 9: Synthesis of N-[(4-hydroxy-1-methyl-7-(3-d-phenoxy)-3-isoquinolinyl)carbonyl]glycine (Compound 46)

Sodium methoxide (351 g, 6.50 mmol) was added to a solution of methyl 4-hydroxy-1-methyl-7-(3-d-phenoxy)-isoquinolin-3-carboxylate (200 mg, 0.65 mmol) and glycine (170 mg, 2.12 mmol) in deuterated methanol-d (4.5 mL) at room temperature, and the reaction solution was sealed in a tube to react at 110° C. overnight. The reaction was cooled to room temperature. The solid was filtered, washed with methanol (cold, 3 mL) and dried. The solid was dissolved in 2 mL of water and extracted with ethyl acetate (3 mL). The aqueous phase was adjusted to acidic pH with acetic acid, and the suspension was stirred at room temperature until a large amount of solid precipitated. The solid was filtered. The cake was washed respectively with water (3×2 mL) and acetone (cold, 2×1 mL) and dried in vacuo to give 137 mg of a white solid. Yield: 59.6%, LC-MS (APCI): m/z=355.2 (M+1); $^1$H NMR (300 MHz, DMSO-$d_6$) (δ/ppm) 13.31 (s, 1H), 12.83 (s, 1H), 9.10 (t, J=5.8 Hz, 1H), 8.29 (d, J=9.0 Hz, 1H), 7.61 (s, 1H), 7.56-7.44 (m, 2H), 4.03 (d, J=6.1 Hz, 2H), 2.70 (s, 3H).

Example 8: Preparation of N-[(4-hydroxy-1-methyl-7-(2,4,6-$d_3$-phenoxy))-3-isoquinolyl) carbonyl]-2,2-$d_2$-glycine (Compound 47)

47

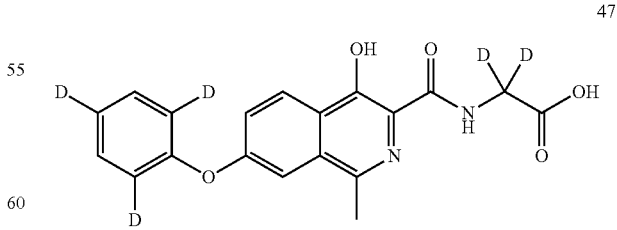

The synthesis method is similar to that of Example 3, except that glycine is replaced with deuterated glycine, and methanol is replaced with deuterated methanol to obtain the final product of compound 47. LC-MS (APCI): m/z=358.4 (M+1); $^1$H NMR (300 MHz, DMSO-$d_6$) (δ/ppm) 13.34 (s, 1H), 9.07 (s, 1H), 8.29 (d, J=9.0 Hz, 1H), 7.62 (d, J=2.3 Hz, 1H), 7.53 (dd, J=9.0, 2.4 Hz, 1H), 7.48 (d, J=4.0 Hz, 2H), 2.70 (s, 3H).

Example 9: Preparation of N-[(4-hydroxy-1-methyl-7-($d_5$-phenoxy))-3-(3-isoquinolinyl) carbonyl]-2,2-$d_2$-glycine (Compound 48)

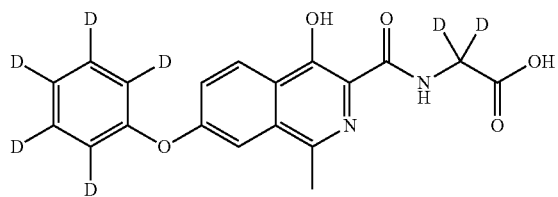

The synthesis method is similar to that of Example 4, except that glycine is replaced by deuterated glycine and methanol is replaced by deuterated methanol to obtain the final product of compound 48. LC-MS (APCI): m/z=360.1 (M+1); $^1$H NMR (300 MHz, DMSO-$d_6$) (δ/ppm) 13.33 (s, 1H), 12.88 (s, 1H), 9.08 (s, 1H), 8.29 (d, J=9.0 Hz, 1H), 7.61 (d, J=2.0 Hz, 1H), 7.52 (dd, J=9.0, 2.2 Hz, 1H), 2.70 (s, 3H).

Example 10: Preparation of N-[(4-hydroxy-1-methyl-7-(3-d-phenoxy)-3-isoquinolinyl) carbonyl]-2,2-$d_2$-glycine (Compound 49)

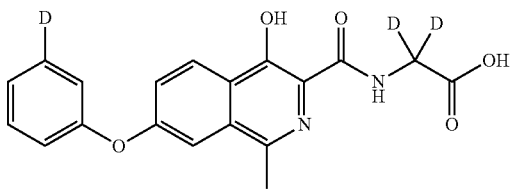

The synthesis method is similar to that of Example 7, except that glycine is replaced by deuterated glycine and methanol is replaced by deuterated methanol to obtain the final product of compound 49. LC-MS (APCI): m/z=355.2 (M+1); $^1$H NMR (300 MHz, DMSO-$d_6$) (δ/ppm) 13.31 (s, 1H), 12.83 (s, 1H), 9.10 (t. J=5.8 Hz, 1H), 8.29 (d, J=9.0 Hz, 1H), 7.61 (s, 1H), 7.56-7.44 (m, 2H), 2.70 (s, 3H).

Biological Activity Test.
Metabolic Stability Evaluation.

Experiments in microsomes: Human liver microsomes: 0.5 mg/mL, Xenotech; Rat liver microsomes: 0.5 mg/mL, Xenotech; Coenzyme (NADPH/NADH): 1 mM, Sigma Life Science; Magnesium chloride: 5 mM, 100 mM phosphate buffer (pH 7.4).

Preparation of stock solution: Powder of the example compound 1-7 was accurately weighed and dissolved in DMSO to 5 mM. Preparation of phosphate buffer (100 mM, pH7.4): A pre-formulated 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4. A NADPH regeneration system solution (containing 6.5 mM NADP, 16.5 mM G-6-P, 3 U/mL G-6-PD, 3.3 mM magnesium chloride) was prepared and placed on wet ice prior to use. Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL human liver microsomes were added, and mixed to obtain a liver microsome dilution solution with a protein concentration of 0.625 mg/mL. 25057.5 μL of phosphate buffer (pH 7.4) was taken into a 50 mL centrifuge tube, to which 812.5 μL SD rat liver microsomes were added, and mixed to obtain a liver microsome dilution solution with a protein concentration of 0.625 mg/mL.

Incubation of the samples: The stock solution of the respective compound was respectively diluted to 0.25 mM with an aqueous solution containing 70% acetonitrile, and used as a working solution, ready for use. 398 μL of the dilution solution of human liver microsomes or rat liver microsome were added to a 96-well incubation plate (N=2), respectively, and 2 μL of 0.25 mM working solution was added and mixed.

Metabolic stability assay: 300 μL of pre-chilled stop solution was added to each well of a 96-well deep well plate and placed on ice as a stop plate. The 96 well incubation plate and NADPH regeneration system were placed in a 37° C. water bath box, shaken at 100 rpm and pre-incubated for 5 min. 80 μL of incubation solution was taken out from each well of the incubation plate and added to the stop plate, mixed, and replenished with 20 μL of NADPH regeneration system solution as a 0-min sample. 80 μL of NADPH regeneration system solution was added to each well of the incubation plate to start the reaction and start counting. The corresponding compound had a reaction concentration of 1 μM and the protein concentration was 0.5 mg/mL. Separately, 100 μL of the reaction solution was taken at 10, 30, and 90 min reaction, respectively, added to a stop plate, and vortexed for 3 minutes to terminate the reaction. The stop plate was centrifuged at 5000×g at 4° C. for 4 min. 100 μL of the supernatant was added to a 96-well plate to which 100 μL of distilled water was previously added, mixed, and analyzed by LC-MS/MS.

Data analysis: The peak areas of the corresponding compound and internal standard were detected by LC-MS/MS system, and the ratio of the peak area of the compound to the internal standard was calculated. The slope was measured by plotting the natural logarithm of the percent of compound remaining versus time, and $t_{1/2}$ and $CL_{int}$ were calculated according to the formula, where V/M is equal to 1/protein concentration.

$$t_{1/2} = -\frac{0.693}{Slope},$$

$$CL_{int} = \frac{0.693}{t_{1/2}} \cdot \frac{V}{M}$$

The experimental results were shown in Table 2 below. Compared to FG4592 (FG-4592 is an oral compound developed by FibroGen, a US biopharmaceutical company, which is in late clinical trials and can be used for treating anemia associated with chronic kidney disease (CKD) and end-stage renal disease (ESRD)), the compounds disclosed herein exhibit excellent metabolic stability in experiments in both human liver microsomes and rat liver microsome.

TABLE 1

Evaluation of Metabolism in liver microsomes for the Compounds of Examples 1-10

| Number | Experiments in human liver microsomes | | Experiments in rat liver microsomes | |
|---|---|---|---|---|
| | $t_{1/2}$(min) | $CL_{int}$ (μL/min/mg) | $t_{1/2}$(min) | $CL_{int}$ (μL/min/mg) |
| FG-4592 | >145 | <8.6 | >145 | <8.6 |
| Compound 11 | — | — | >145 | <8.6 |
| Compound 13 | >145 | <8.6 | >145 | <8.6 |
| Compound 23 | >145 | <8.6 | >145 | <8.6 |
| Compound 32 | >145 | <8.6 | >145 | <8.6 |
| Compound 34 | — | — | >145 | <8.6 |
| Compound 36 | >145 | <8.6 | >145 | <8.6 |
| Compound 46 | >145 | <8.6 | >145 | <8.6 |
| Compound 47 | >145 | <8.6 | >145 | <8.6 |
| Compound 48 | >145 | <8.6 | >145 | <8.6 |
| Compound 49 | >145 | <8.6 | >145 | <8.6 |

Pharmacokinetic Evaluation in Rats.

6 male Sprague-Dawley rats (7-8 weeks old, and weighing approximately 210 g) were divided into 2 groups with 3 rats in each group. The rats were intravenously or orally administered a single dose of compound (3 mg/kg intravenously, 10 mg/kg orally) to compare pharmacokinetic differences.

The rats were raised on standard food and water. Fasting was started 16 hours before the test. The drug was dissolved with PEG400 and dimethyl sulfoxide. The blood samples were collected from eyelids at the time points of 0.083 hours, 0.25 hours, 0.5 hours, 1 hour, 2 hours, 4 hours, 6 hours, 8 hours, 12 hours, and 24 hours after administration.

Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at a later time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound of the present disclosure in plasma was determined by LC-MS/MS. The pharmacokinetic parameters were calculated based on the blood concentration of each animal at different time points.

The results of the experiment were shown in Table 3 below. Compared with the control compound FG-4592, the oral availability of the compound 11, compound 32, and compound 49 disclosed herein was greatly increased, indicating that the oral administration has better pharmacokinetics in animals, and thus has better pharmacodynamics and therapeutic effects.

TABLE 2

Rat pharmacokinetics experiment

| PK parameters | FG-4592 | | Compound 11 | | Compound 32 | | Compound 49 | |
|---|---|---|---|---|---|---|---|---|
| | IV | PO | IV | PO | IV | PO | IV | PO |
| $T_{max}$ (h) | 0.08 | 2.83 | 0.08 | 4.00 | 0.75 | 0.83 | 0.08 | 2.67 |
| $C_{max}$ (h) | 21145.4 | 22073.5 | 19030.8 | 24603.7 | 12203.9 | 17733.2 | 19504.8 | 25358.2 |
| $AUC_{0-t}$ (h*ng/mL) | 63771.7 | 196009.4 | 51563.7 | 259823.3 | 55904.9 | 184587.2 | 49376.4 | 217985.6 |
| $AUC_{0-\infty}$ (h*ng/mL) | 63810.0 | 196407.7 | 51608.4 | 260986.4 | 55941.5 | 184927.8 | 49454.9 | 222071.6 |
| $MRT_{INF\_pred}$ (h) | 2.82 | 5.03 | 2.84 | 5.87 | 3.14 | 5.33 | 2.85 | 5.83 |
| $Vz_{\_pred}$ (L/kg) | 0.15 | 0.20 | 0.21 | 0.16 | 0.18 | 0.21 | 0.25 | 0.24 |
| $Cl_{\_pred}$ (L/kg) | 0.05 | 0.05 | 0.06 | 0.04 | 0.05 | 0.06 | 0.06 | 0.05 |
| $T_{1/2}$ (h) | 2.08 | 2.78 | 2.43 | 2.77 | 2.49 | 2.43 | 2.89 | 3.33 |
| F (%) | 92.21 | | 151.17 | | 99.05 | | 132.44 | |

It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

The above content is a further detailed description disclosed herein in combination with specific preferred embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

What is claimed is:

1. A compound represented by Formula (I), or a pharmaceutically acceptable salt thereof,

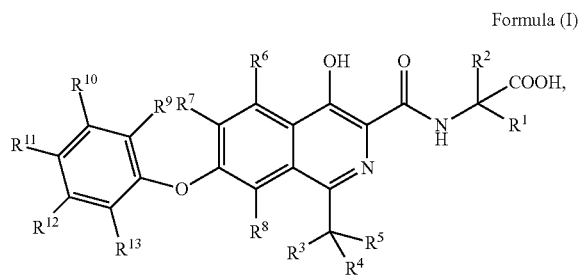

Formula (I)

wherein:
$R^1$, $R^2$, $R^4$, $R^5$, $R^9$, $R^{10}$, $R^{11}$, $R^{12}$, and $R^{13}$ are each independently hydrogen or deuterium; and
$R^3$, $R^6$, $R^7$, and $R^8$ are each hydrogen;
provided that at least one of $R^1$, $R^2$, $R^4$, $R^5$, $R^9$, $R^{10}$, $R^{11}$, $R^{12}$, and $R^{13}$ is deuterium.

2. The compound according to claim 1 or a pharmaceutically acceptable salt thereof, wherein $R^9$, $R^{10}$, $R^{11}$, $R^{12}$, and $R^{13}$ are each hydrogen.

3. The compound according to claim 1 or a pharmaceutically acceptable salt thereof, wherein $R^1$ and $R^2$ are each deuterium.

4. The compound according to claim 2 or a pharmaceutically acceptable salt thereof, wherein $R^1$ and $R^2$ are each deuterium.

5. A pharmaceutical composition, characterized in that it comprises a pharmaceutically acceptable carrier and the compound according to claim 1 or a pharmaceutically acceptable salt thereof.

6. A compound or a pharmaceutically acceptable salt thereof, wherein the compound is of the formula:

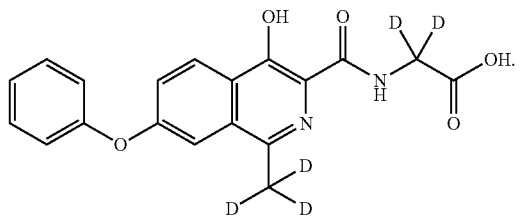 [SMILES: [2H]C([2H])(NC(=O)c1nc(C([2H])([2H])[2H])c2cc(Oc3ccccc3)ccc2c1O)C(=O)O]

7. A compound or a pharmaceutically acceptable salt thereof, wherein the compound is of the formula:

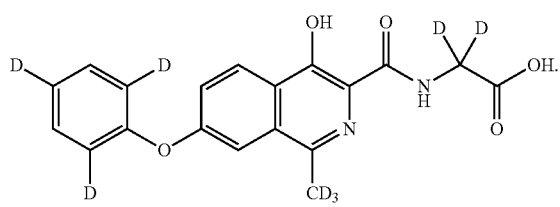 [SMILES: [2H]c1cc([2H])c(Oc2ccc3c(O)c(C(=O)NC([2H])([2H])C(=O)O)nc(C([2H])([2H])[2H])c3c2)c([2H])c1]

8. A pharmaceutical composition, characterized in that it comprises a pharmaceutically acceptable carrier and the compound according to claim 6 or a pharmaceutically acceptable salt thereof.

9. A pharmaceutical composition, characterized in that it comprises a pharmaceutically acceptable carrier and the compound according to claim 7 or a pharmaceutically acceptable salt thereof.

10. The compound according to claim 1 or a pharmaceutically acceptable salt thereof, wherein the compound is of the formula:

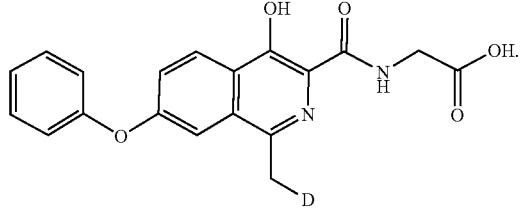 [SMILES: [2H]Cc1nc(C(=O)NCC(=O)O)c(O)c2ccc(Oc3ccccc3)cc12]

11. The compound according to claim 1 or a pharmaceutically acceptable salt thereof, wherein the compound is of the formula:

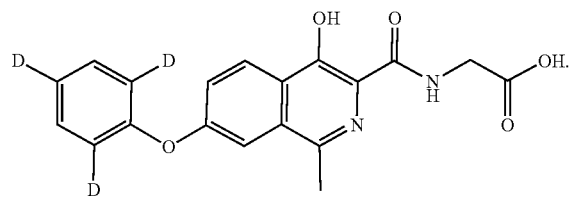 [SMILES: [2H]c1cc([2H])c(Oc2ccc3c(O)c(C(=O)NCC(=O)O)nc(C)c3c2)c([2H])c1]

12. The compound according to claim 1 or a pharmaceutically acceptable salt thereof, wherein the compound is of the formula:

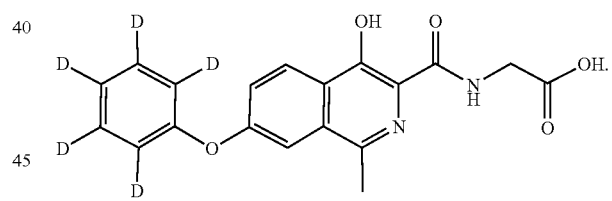

13. The compound according to claim 1 or a pharmaceutically acceptable salt thereof, wherein the compound is of the formula:

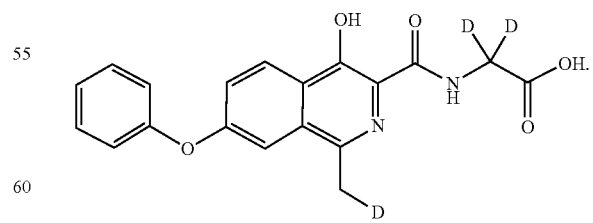

14. The compound according to claim 1 or a pharmaceutically acceptable salt thereof, wherein the compound is of the formula:

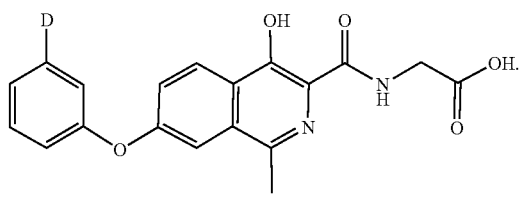 [SMILES: [2H]c1cccc(Oc2ccc3c(O)c(C(=O)NCC(=O)O)nc(C)c3c2)c1]

15. The compound according to claim 1 or a pharmaceutically acceptable salt thereof, wherein the compound is of the formula:

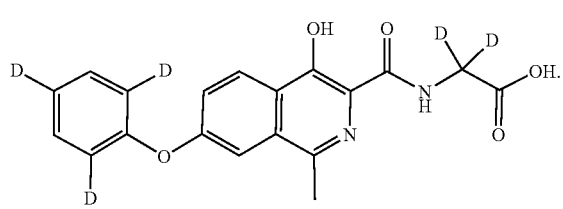 [SMILES: [2H]c1cc([2H])c(Oc2ccc3c(O)c(C(=O)NC([2H])([2H])C(=O)O)nc(C)c3c2)c([2H])c1]

16. The compound according to claim 1 or a pharmaceutically acceptable salt thereof, wherein the compound is of the formula:

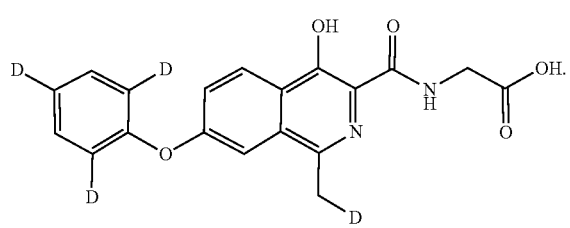 [SMILES: [2H]Cc1nc(C(=O)NCC(=O)O)c(O)c2ccc(Oc3c([2H])cc([2H])cc3[2H])cc12]

17. The compound according to claim 1 or a pharmaceutically acceptable salt thereof, wherein the compound is of the formula:

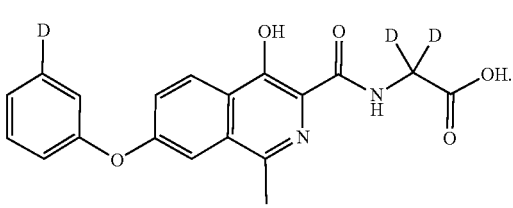 [SMILES: [2H]c1cccc(Oc2ccc3c(O)c(C(=O)NC([2H])([2H])C(=O)O)nc(C)c3c2)c1]

18. The compound according to claim 1 or a pharmaceutically acceptable salt thereof, wherein the compound is of the formula:

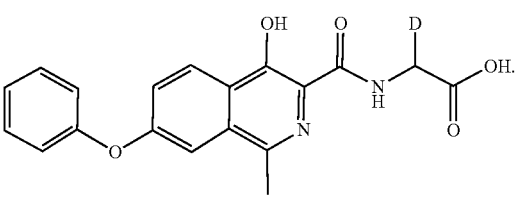 [SMILES: [2H]C(NC(=O)c1nc(C)c2cc(Oc3ccccc3)ccc2c1O)C(=O)O]

19. The compound according to claim 1 or a pharmaceutically acceptable salt thereof, wherein the compound is of the formula:

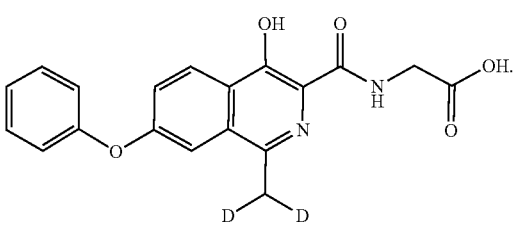 [SMILES: [2H]C([2H])c1nc(C(=O)NCC(=O)O)c(O)c2ccc(Oc3ccccc3)cc12]

\* \* \* \* \*